(12) United States Patent
Flores et al.

(10) Patent No.: US 10,576,247 B2
(45) Date of Patent: Mar. 3, 2020

(54) INTRABODY SURGICAL FLUID TRANSFER ASSEMBLIES WITH ADJUSTABLE EXPOSED CANNULA TO NEEDLE TIP LENGTH, RELATED SYSTEMS AND METHODS

(71) Applicant: MRI Interventions, Inc., Irvine, CA (US)

(72) Inventors: Jesse Flores, Perris, CA (US); Peter G. Piferi, Orange, CA (US)

(73) Assignee: MRI Interventions, Inc., Irvine, CA (US)

(*) Notice: Subject to any disclaimer, the term of this patent is extended or adjusted under 35 U.S.C. 154(b) by 406 days.

(21) Appl. No.: 15/420,685

(22) Filed: Jan. 31, 2017

(65) Prior Publication Data
US 2017/0232229 A1 Aug. 17, 2017

Related U.S. Application Data

(60) Provisional application No. 62/382,434, filed on Sep. 1, 2016, provisional application No. 62/296,323, filed on Feb. 17, 2016.

(51) Int. Cl.
*A61M 25/00* (2006.01)
*A61M 39/10* (2006.01)
*A61B 90/11* (2016.01)

(52) U.S. Cl.
CPC ......... *A61M 25/0084* (2013.01); *A61B 90/11* (2016.02); *A61M 25/0023* (2013.01);
(Continued)

(58) Field of Classification Search
CPC .......... A61M 25/0084; A61M 25/0023; A61M 25/0097; A61M 39/10; A61M 2025/0089; A61B 90/11
See application file for complete search history.

(56) References Cited

U.S. PATENT DOCUMENTS 3,540,447 A 11/1970 Howe
3,824,157 A 7/1974 Macur
(Continued)

FOREIGN PATENT DOCUMENTS

CA 2655515 8/2010
EP 1029509 8/2000
(Continued)

OTHER PUBLICATIONS

International Search Report and the Written Opinion of the International Searching Authority corresponding to International Patent Application No. PCT/US2017/015581 (17 pages) (dated May 31, 2017).

(Continued)

*Primary Examiner* — Lauren P Farrar
(74) *Attorney, Agent, or Firm* — Myers Bigel, P.A.

(57) ABSTRACT

Devices for transferring fluid to or from a subject include an elongate tubular cannula having opposing proximal and distal ends with an axially extending lumen. The devices also include an elongate needle having opposing proximal and distal ends. The elongate needle is configured so that the distal end of the needle extends out of the distal end of the cannula a suitable adjustable distance. The devices also include a housing with a length adjustment mechanism that adjusts a length between the tip of the needle and the distal end of the tubular cannula.

24 Claims, 25 Drawing Sheets

(52) U.S. Cl.
CPC ........ *A61M 25/0097* (2013.01); *A61M 39/10* (2013.01); *A61M 2025/0089* (2013.01)

(56) References Cited

U.S. PATENT DOCUMENTS

| | | | |
|---|---|---|---|
| 3,856,009 A | 12/1974 | Winnie | |
| 4,149,535 A | 4/1979 | Volder | |
| 4,239,042 A | 12/1980 | Asai | |
| 4,265,928 A | 5/1981 | Braun | |
| 4,327,722 A | 5/1982 | Groshong et al. | |
| 4,449,532 A | 5/1984 | Storz | |
| 4,531,943 A | 7/1985 | Van Tassel et al. | |
| 4,543,091 A | 9/1985 | Froning et al. | |
| 4,543,092 A | 9/1985 | Mehler et al. | |
| 4,597,421 A | 7/1986 | Wells | |
| 4,623,789 A | 11/1986 | Ikeda et al. | |
| 4,629,450 A | 12/1986 | Suzuki et al. | |
| 4,705,511 A | 11/1987 | Kocak | |
| 4,738,658 A | 4/1988 | Magro et al. | |
| 4,739,768 A | 4/1988 | Engelson | |
| 4,781,691 A | 11/1988 | Gross | |
| 4,820,349 A | 4/1989 | Saab | |
| 4,846,799 A | 7/1989 | Tanaka et al. | |
| 4,897,077 A | 1/1990 | Cicciu et al. | |
| 4,955,863 A | 9/1990 | Walker et al. | |
| 4,978,334 A | 12/1990 | Toye et al. | |
| 4,995,866 A | 2/1991 | Amplatz et al. | |
| 5,069,673 A | 12/1991 | Shwab | |
| 5,380,292 A | 1/1995 | Wilson | |
| 5,562,626 A | 10/1996 | Sanpietro | |
| 5,699,801 A | 12/1997 | Atalar et al. | |
| 5,720,720 A | 2/1998 | Laske et al. | |
| 5,722,985 A | 3/1998 | Pettus | |
| 5,792,144 A | 8/1998 | Fischell et al. | |
| 5,833,662 A | 11/1998 | Stevens | |
| 5,851,203 A | 12/1998 | van Muiden | |
| 5,857,999 A | 1/1999 | Quick et al. | |
| 5,871,470 A | 2/1999 | McWha | |
| 5,902,282 A | 5/1999 | Balbierz | |
| 5,919,171 A | 7/1999 | Kira et al. | |
| 5,928,145 A | 7/1999 | Ocali et al. | |
| 5,935,122 A * | 8/1999 | Fourkas | A61M 25/005 604/249 |
| 6,020,196 A | 2/2000 | Hu et al. | |
| 6,026,316 A | 2/2000 | Kucharczyk et al. | |
| 6,030,369 A | 2/2000 | Engelson et al. | |
| 6,042,579 A | 3/2000 | Elsberry et al. | |
| 6,050,992 A | 4/2000 | Nichols | |
| 6,093,180 A | 7/2000 | Elsberry | |
| 6,167,311 A | 12/2000 | Rezai | |
| 6,186,986 B1 | 2/2001 | Berg et al. | |
| 6,231,591 B1 | 5/2001 | Desai | |
| 6,263,229 B1 | 7/2001 | Atalar et al. | |
| 6,284,971 B1 | 9/2001 | Atalar et al. | |
| RE37,410 E | 10/2001 | Brem et al. | |
| 6,309,634 B1 | 10/2001 | Bankiewicz et al. | |
| 6,336,915 B1 | 1/2002 | Scarfone et al. | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,461,296 B1 | 10/2002 | Desai | |
| 6,524,299 B1 | 2/2003 | Tran et al. | |
| 6,526,318 B1 | 2/2003 | Ansarinia | |
| 6,533,751 B2 | 3/2003 | Cragg et al. | |
| 6,539,263 B1 | 3/2003 | Schiff et al. | |
| 6,551,290 B1 | 4/2003 | Elsberry et al. | |
| 6,585,694 B1 * | 7/2003 | Smith | A61M 25/0084 600/563 |
| 6,606,513 B2 | 8/2003 | Lardo et al. | |
| 6,609,030 B1 | 8/2003 | Rezai et al. | |
| 6,628,980 B2 | 9/2003 | Atalar et al. | |
| 6,641,555 B1 | 11/2003 | Botich et al. | |
| 6,641,564 B1 | 11/2003 | Kraus | |
| 6,675,033 B1 | 1/2004 | Lardo et al. | |
| 6,689,142 B1 | 2/2004 | Tremaglio, Jr. et al. | |
| 6,701,176 B1 | 3/2004 | Halperin et al. | |
| 6,708,064 B2 | 3/2004 | Rezai | |
| 6,904,307 B2 | 6/2005 | Karmarkar et al. | |
| 7,037,295 B2 | 5/2006 | Tiernan et al. | |
| 7,182,944 B2 | 2/2007 | Bankiewicz | |
| 7,329,262 B2 | 2/2008 | Gill | |
| 7,341,577 B2 | 3/2008 | Gill | |
| 7,351,239 B2 | 4/2008 | Gill | |
| 7,371,225 B2 | 5/2008 | Oldfield et al. | |
| 7,780,692 B2 | 8/2010 | Nance et al. | |
| 7,815,623 B2 | 10/2010 | Bankiewicz et al. | |
| 7,892,203 B2 | 2/2011 | Lenker et al. | |
| 7,951,110 B2 | 5/2011 | Bishop et al. | |
| 8,128,600 B2 | 3/2012 | Gill | |
| 8,175,677 B2 | 5/2012 | Sayler et al. | |
| 8,195,272 B2 | 6/2012 | Piferi et al. | |
| 8,315,689 B2 | 11/2012 | Jenkins et al. | |
| 8,340,743 B2 | 12/2012 | Jenkins et al. | |
| 8,348,892 B2 | 1/2013 | Lenker et al. | |
| 8,374,677 B2 | 2/2013 | Piferi et al. | |
| 8,597,277 B2 | 12/2013 | Lenker et al. | |
| 8,827,987 B2 | 9/2014 | Fielder et al. | |
| 8,900,214 B2 | 12/2014 | Nance et al. | |
| 9,044,577 B2 | 6/2015 | Bishop et al. | |
| 9,050,419 B2 | 6/2015 | Farnan | |
| 9,452,241 B2 | 9/2016 | Gill et al. | |
| 9,610,048 B2 | 4/2017 | Vij et al. | |
| 9,891,296 B2 | 2/2018 | Piferi | |
| 10,105,485 B2 | 10/2018 | Piferi et al. | |
| 2002/0087152 A1 | 7/2002 | Mikus et al. | |
| 2002/0091372 A1 | 7/2002 | Cragg et al. | |
| 2002/0095081 A1 | 7/2002 | Vilsmeier | |
| 2002/0114780 A1 | 8/2002 | Bankiewicz et al. | |
| 2002/0141980 A1 | 10/2002 | Bankiewicz et al. | |
| 2002/0183763 A1 | 12/2002 | Callol et al. | |
| 2003/0028095 A1 | 2/2003 | Tulley et al. | |
| 2003/0050557 A1 | 3/2003 | Susil et al. | |
| 2003/0073934 A1 | 4/2003 | Putz | |
| 2003/0130575 A1 | 7/2003 | Desai | |
| 2003/0216714 A1 | 11/2003 | Gill | |
| 2004/0044329 A1 * | 3/2004 | Trudell | A61B 17/3478 604/507 |
| 2004/0046557 A1 | 3/2004 | Karmarkar et al. | |
| 2004/0064098 A1 | 4/2004 | Cuschieri et al. | |
| 2004/0092879 A1 | 5/2004 | Kraus et al. | |
| 2004/0199129 A1 | 10/2004 | DiMatteo | |
| 2004/0209810 A1 | 10/2004 | Gill et al. | |
| 2004/0215162 A1 | 10/2004 | Putz | |
| 2004/0249261 A1 | 12/2004 | Torchia et al. | |
| 2005/0004504 A1 | 1/2005 | Frye et al. | |
| 2005/0112065 A1 | 5/2005 | Drummond et al. | |
| 2005/0148865 A1 | 7/2005 | Weber | |
| 2005/0154297 A1 | 7/2005 | Gill | |
| 2005/0256503 A1 | 11/2005 | Hall | |
| 2006/0052750 A1 | 3/2006 | Lenker et al. | |
| 2006/0073101 A1 | 4/2006 | Oldfield et al. | |
| 2006/0129126 A1 | 6/2006 | Kaplitt et al. | |
| 2006/0135945 A1 | 6/2006 | Bankiewicz et al. | |
| 2006/0217664 A1 | 9/2006 | Hattler et al. | |
| 2007/0088295 A1 | 4/2007 | Bankiewicz | |
| 2007/0110798 A1 | 5/2007 | Drummond et al. | |
| 2007/0167736 A1 | 7/2007 | Dietz et al. | |
| 2007/0179455 A1 | 8/2007 | Geliebter et al. | |
| 2007/0250021 A1 | 10/2007 | Brimhall et al. | |
| 2007/0254842 A1 | 11/2007 | Bankiewicz | |
| 2008/0103456 A1 * | 5/2008 | Johnson | A61B 5/6864 604/264 |
| 2008/0119821 A1 | 5/2008 | Agnihotri et al. | |
| 2008/0215008 A1 | 9/2008 | Nance et al. | |
| 2008/0228168 A1 | 9/2008 | Mittermeyer et al. | |
| 2008/0319377 A1 | 12/2008 | Keenan | |
| 2009/0088695 A1 | 4/2009 | Kapur et al. | |
| 2009/0088730 A1 | 4/2009 | Hoofnagle et al. | |
| 2009/0112084 A1 | 4/2009 | Piferi et al. | |
| 2009/0118610 A1 | 5/2009 | Karmarkar et al. | |
| 2009/0143764 A1 | 6/2009 | Nelson | |
| 2009/0171184 A1 | 7/2009 | Jenkins et al. | |
| 2009/0198218 A1 | 8/2009 | Gill et al. | |
| 2009/0209937 A1 | 8/2009 | Rogawski et al. | |

(56) References Cited

U.S. PATENT DOCUMENTS

| | | | |
|---|---|---|---|
| 2009/0281453 | A1 | 11/2009 | Tsonton et al. |
| 2010/0130958 | A1 | 5/2010 | Kang et al. |
| 2010/0198052 | A1 | 8/2010 | Jenkins et al. |
| 2010/0217236 | A1 | 8/2010 | Gill et al. |
| 2010/0228122 | A1 | 9/2010 | Keenan et al. |
| 2010/0317961 | A1 | 12/2010 | Jenkins et al. |
| 2010/0318061 | A1* | 12/2010 | Derrick ............. A61L 29/106 604/508 |
| 2010/0318064 | A1 | 12/2010 | Derrick et al. |
| 2011/0282319 | A1 | 11/2011 | Gill |
| 2012/0123391 | A1 | 5/2012 | Gill et al. |
| 2012/0310182 | A1 | 12/2012 | Fielder et al. |
| 2013/0006095 | A1* | 1/2013 | Jenkins ............. A61B 5/7435 600/411 |
| 2013/0030408 | A1 | 1/2013 | Piferi et al. |
| 2014/0257168 | A1 | 9/2014 | Gill |
| 2014/0343500 | A1 | 11/2014 | Fielder et al. |
| 2015/0374908 | A1 | 12/2015 | Piferi |
| 2016/0346505 | A1 | 12/2016 | Gill et al. |
| 2017/0197017 | A1 | 7/2017 | Martin |
| 2018/0303560 | A1 | 10/2018 | Pandey et al. |

FOREIGN PATENT DOCUMENTS

| | | |
|---|---|---|
| EP | 1 334 740 A1 | 8/2003 |
| EP | 1 482 851 A1 | 12/2004 |
| EP | 1 491 154 A1 | 12/2004 |
| GB | 1 255 551 | 12/1971 |
| JP | 2002-509767 A | 4/2002 |
| JP | 2004-147830 A | 5/2004 |
| WO | WO 99/04849 A1 | 2/1999 |
| WO | WO 99/49909 A2 | 10/1999 |
| WO | WO 02/053205 A2 | 7/2002 |
| WO | WO 03/077785 A1 | 9/2003 |
| WO | WO 2004/031348 A2 | 4/2004 |
| WO | WO 2008/020237 A2 | 2/2008 |
| WO | WO 2008/020241 A2 | 2/2008 |
| WO | WO 2008/144585 A1 | 11/2008 |
| WO | WO 2008/144775 A1 | 11/2008 |
| WO | WO 2009/042135 A2 | 4/2009 |
| WO | WO 2009/047490 A2 | 4/2009 |
| WO | WO 2009/066130 A1 | 5/2009 |
| WO | WO 2009/101397 A1 | 8/2009 |
| WO | WO 2010/040970 A2 | 4/2010 |
| WO | WO 2011/098768 A1 | 8/2011 |
| WO | WO 2011/098769 A1 | 8/2011 |
| WO | WO 2012/178169 A2 | 12/2012 |
| WO | WO 2013/050148 A1 | 4/2013 |
| WO | WO 2014/089373 A1 | 6/2014 |

OTHER PUBLICATIONS

Bankiewicz et al. "Convection-Enhanced Delivery of AAV Vector in Parkinsonian Monkeys; In Vivo Detection of Gene Expression and Restoration of Dopaminergic Function Using Pro-drug Approach" *Experimental Neurology* 164:2-14 (2000).

Chen et al. "Variables affecting convection-enhanced delivery to the striatum: a systematic examination of rate of infusion, cannula size, infusate concentration, and tissue-cannula sealing time" *Journal of Neurosurgery* 90:315-320 (1999).

Chen et al. "Combination Therapy with Irinotecan and Protein Kinase C Inhibitors in Malignant Glioma" *Cancer* 97(9 Suppl):2363-2373 (2003).

Chen et al. "Surface properties, more than size, limiting convective distribution of virus-sized particles and viruses in the central nervous system" *Journal of Neurosurgery* 103:311-319 (2005).

Cunningham et al. "Distribution of AAV-TK following intracranial convection-enhanced delivery into rats" *Cell Transplantation* 9(5):585-594 (2000) (Abstract Only).

Groothuis, Dennis R. "The blood-brain and blood-tumor barriers: A review of strategies for increasing drug delivery" *Neuro-Oncology* 2:45-59 (2000).

Hadaczek et al. "Convection-Enhanced Delivery of Adeno-Associated Virus Type 2 (AAV2) into the Striatum and Transport of AAV2 Within Monkey Brain" *Human Gene Therapy* 17:291-302 (2006).

Hadaczek et al. "The 'Perivascular Pump' Driven by Arterial Pulsation is a Powerful Mechanism for the Distribution of Therapeutic molecules within the Brain" *Molecular Therapy* 14(1):69-78 (2006).

Krauze et al. "Reflux-free cannula for convection-enhanced high-speed delivery of therapeutic agents" *Journal of Neurosurgery* 103:923-929 (2005).

Krauze et al. "Real-time Imaging and Quantification of Brain Delivery of Liposomes" *Pharmaceutical Research* 23(11):2493-2504 (2006).

Laske et al. "Chronic interstitial infusion of protein to primate brain: determination of drug distribution and clearance with single-photon emission computerized tomography imaging" *Journal of Neurosurgery* 87:586-594 (1997).

Lieberman et al. "Convection-enhanced distribution of large molecules in gray matter during interstitial drug infusion" *Journal of Neurosurgery* 82:1021-1029 (1995).

Lonser et al. "Successful and safe perfusion of the primate brainstem: in vivo magnetic resonance imaging of macromolecular distribution during infusion" *Journal of Neurosurgery* 97:905-913 (2002).

Mamot et al. "Extensive distribution of liposomes in rodent brains and brain tumors following convection-enhanced delivery" *Journal of Neuro-Oncology* 68:1-9 (2004).

Mardor et al. "Monitoring Response to Convection-enhanced Taxol Delivery in Brain Tumor Patients Using Diffusion-weighted Magnetic Resonance Imaging" *Cancer Research* 61:4971-4973 (2001).

Marshall et al. "Biocompatibility of Cardiovascular Gene Delivery Catheters with Adenovirus Vectors: An Important Determinant of the Efficiency of Cardiovascular Gene Transfer" *Molecular Therapy* 1(5):423-429 (2000).

Morrison et al. "High-flow microinfusion: tissue penetration and pharmacodynamics" *American Journal of Physiology—Regulatory, Integrative and Comparative Physiology* 266:R292-R305 (1994).

Morrison et al. "Focal delivery during direct infusion to brain: role of flow rate, catheter diameter, and tissue mechanics" *American Journal of Physiology—Regulatory, Integrative and Comparative Physiology* 277:R1218-R1229 (1999).

Naimark et al. "Adenovirus-Catheter Compatibility Increases Gene Expression After Delivery to Porcine Myocardium" *Human Gene Therapy* 14:161-166 (2003).

Pardridge, William M. "Drug Delivery to the Brain" *Journal of Cerebral Blood Flow and Metabolism* 17:713-731 (1997).

Pardridge, William M. "The Blood-Brain Barrier: Bottleneck in Brain Drug Development" *NeuroRx: The Journal of the American Society for Experimental Neuro Therapeutics* 2:3-14 (2005).

Patel et al. "Intraputamenal Infusion of Glial Cell Line-Derived Neurotrophic Factor in PD: A Two-Year Outcome Study" *Annals of Neurology* 57:298-302 (2005).

Qureshi et al. "Multicolumn Infusion of Gene Therapy Cells into Human Brain Tumors: Technical Report" *Neurosurgery* 46(3):663-669 (2000) (Abstract Only).

Richardson et al. "Interventional MRI-guided Putaminal Delivery of AAV2-GDNF for a Planned Clinical Trial in Parkinson's Disease" *Molecular Therapy* 19(6):1048-1057 (2011).

Rogawski, Michael A. "Convection-Enhanced Delivery in the Treatment of Epilepsy" *Neurotherapeutics: The Journal of the American Society for Experimental NeuroTherapeutics* 6:344-351 (2009).

Saito et al. "Convection-Enhanced Delivery of Tumor Necrosis Factor-Related Apoptosis-Inducing Ligand with Systemic Administration of Temozolomide Prolongs Survival in an Intracranial Glioblastoma Xenograft Model" *Cancer Research* 64:6858-6862 (2004).

Saito et al. "Distribution of Liposomes into Brain and Rat Brain Tumor Models by Convection-Enhanced Delivery Monitored with Magnetic Resonance Imaging" *Cancer Research* 64:2572-2579 (2004).

Tsui et al. "Stability of Adenoviral Vectors Following Catheter Delivery" *Molecular Therapy* 3(1):122-125 (2001).

(56) References Cited

OTHER PUBLICATIONS

Vogelbaum, Michael A. "Convection enhanced delivery for the treatment of malignant gliomas: symposium review" *Journal of Neuro-Oncology* 73:57-69 (2005).

Westphal et al. "Perspectives of cellular and molecular neurosurgery" *Journal of Neuro-Oncology* 70:255-269 (2004).

\* cited by examiner

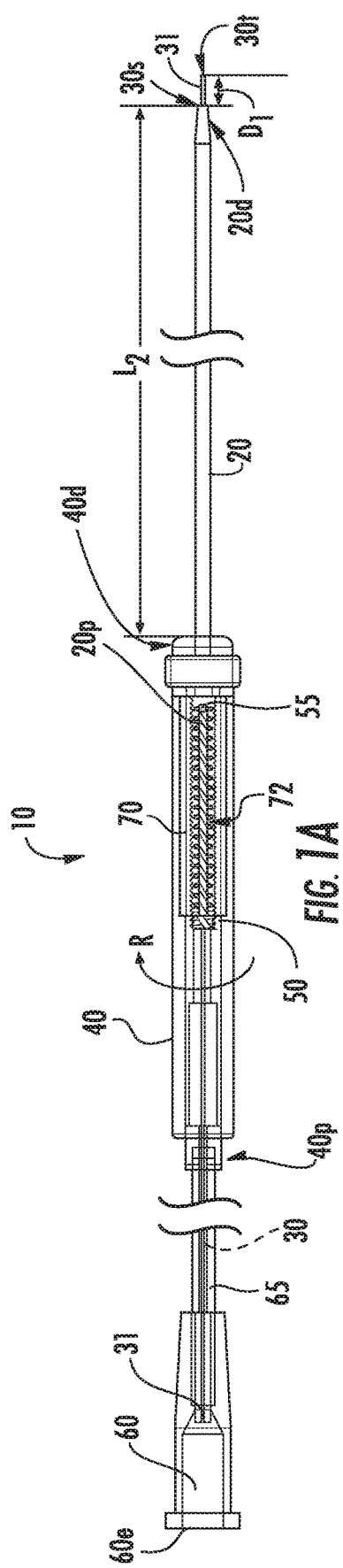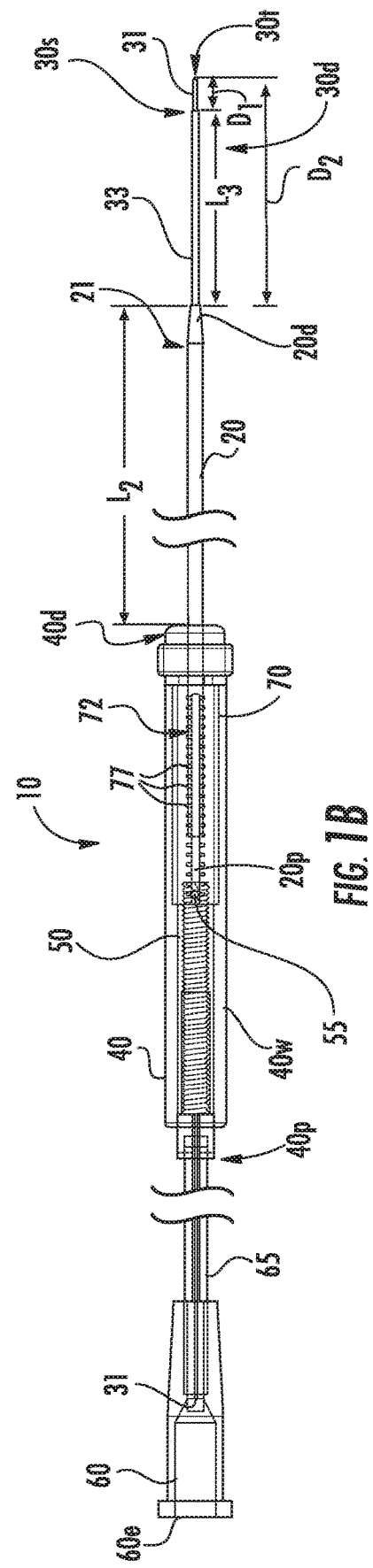

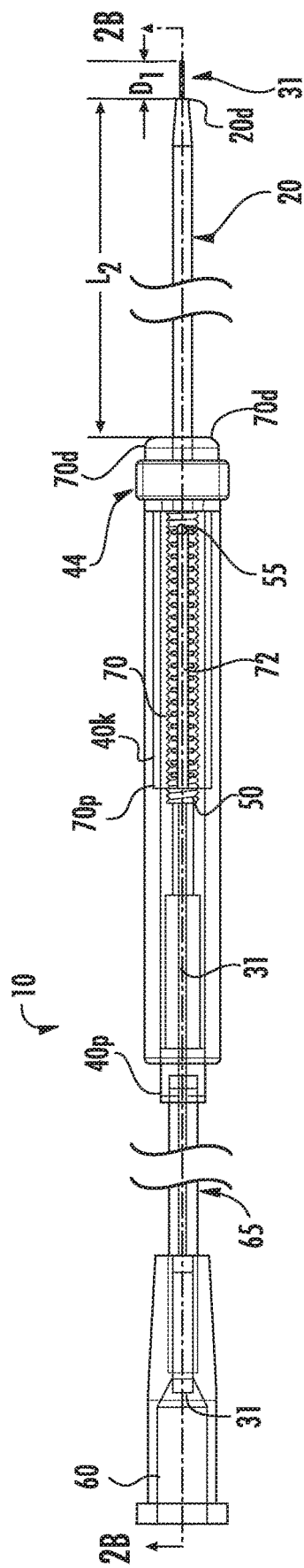
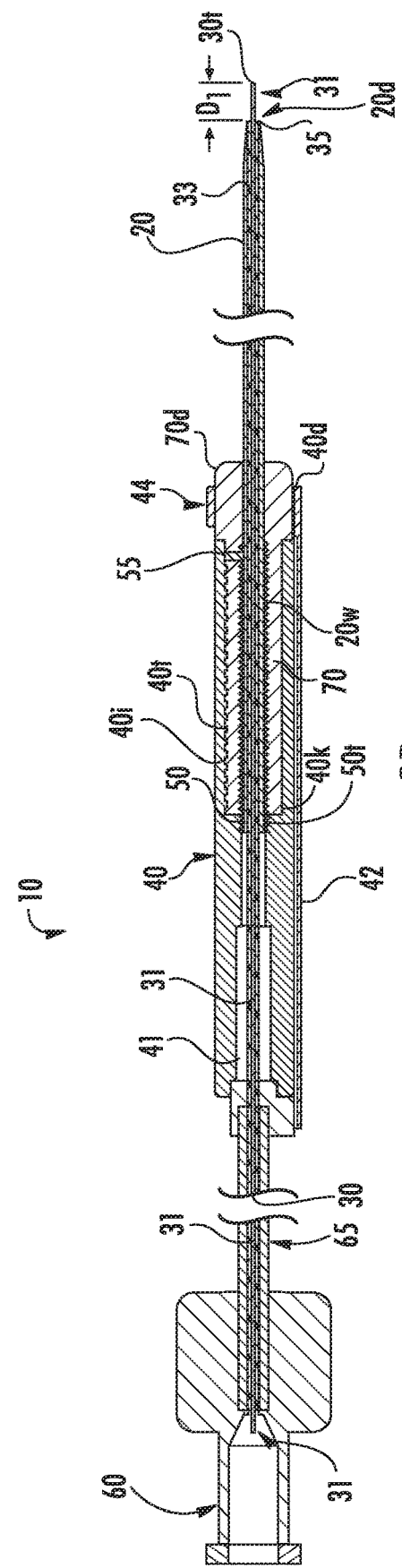
FIG. 2A
FIG. 2B

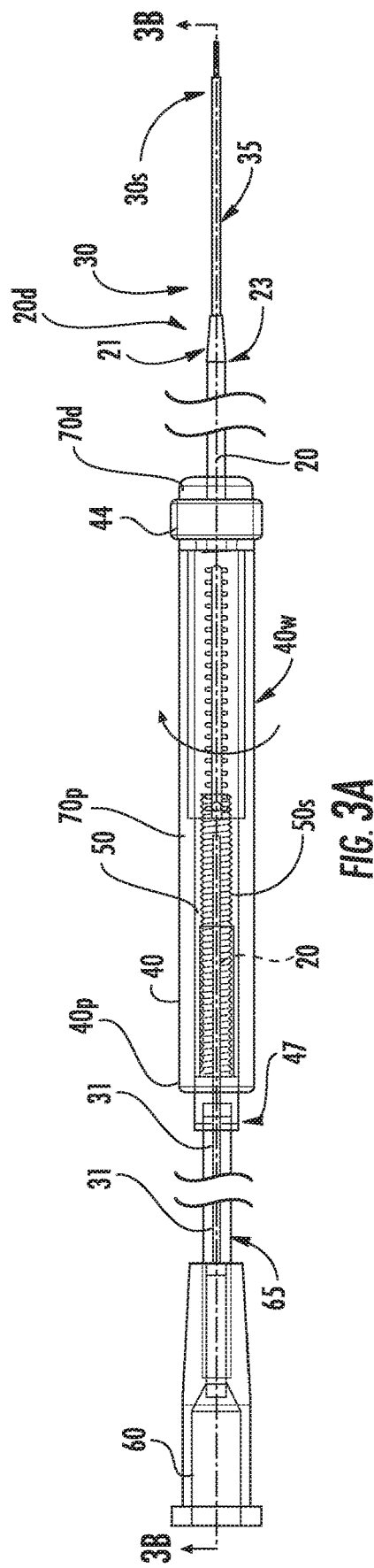
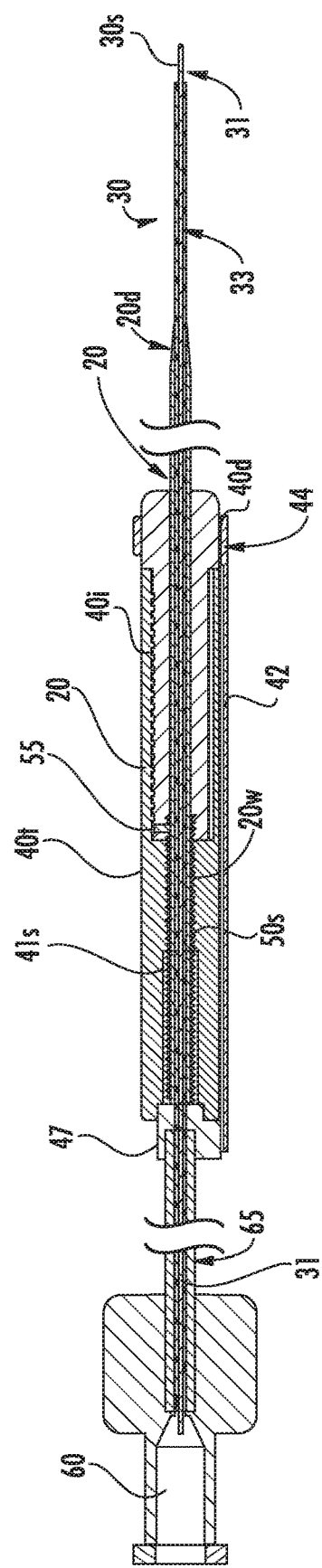
FIG. 3A
FIG. 3B

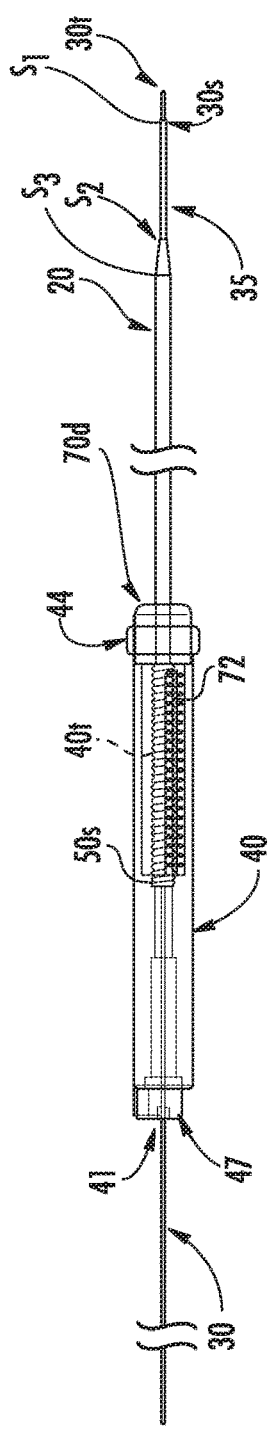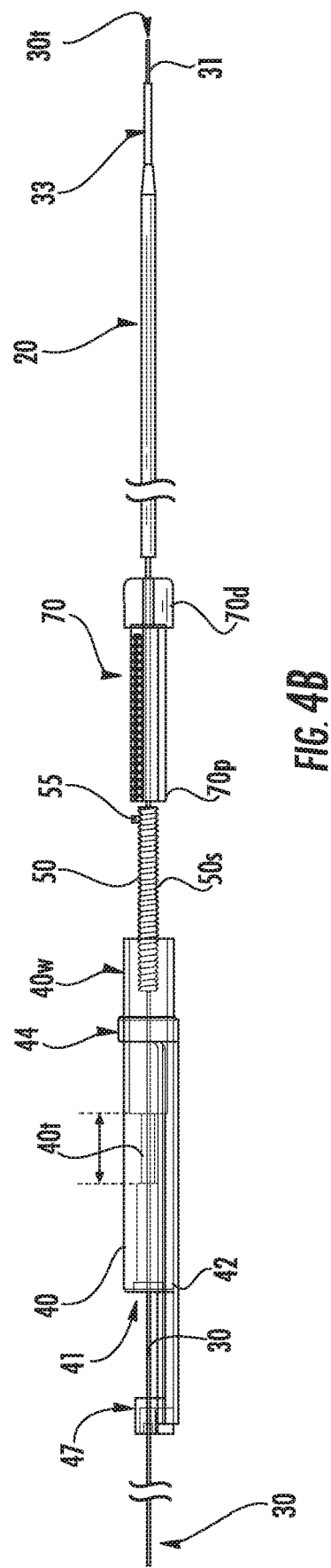
FIG. 4A
FIG. 4B

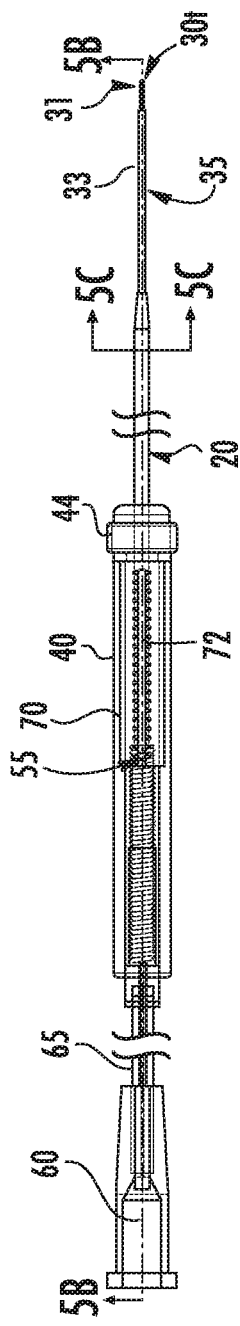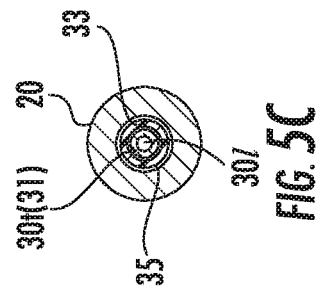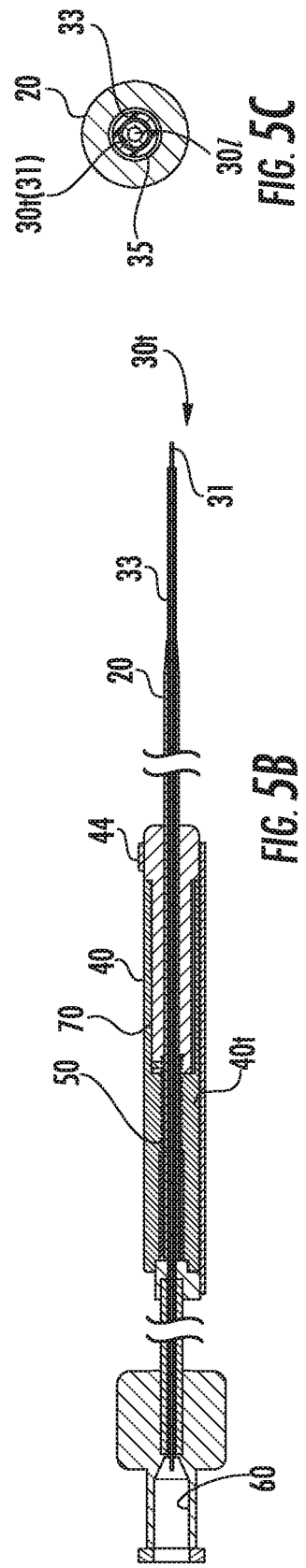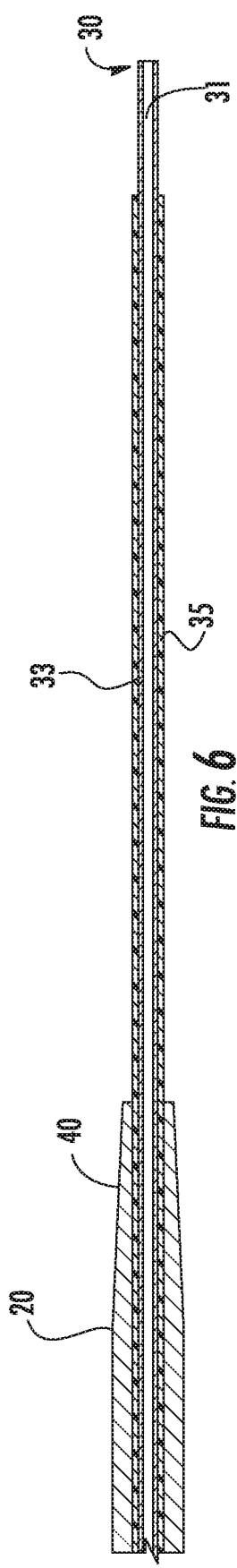

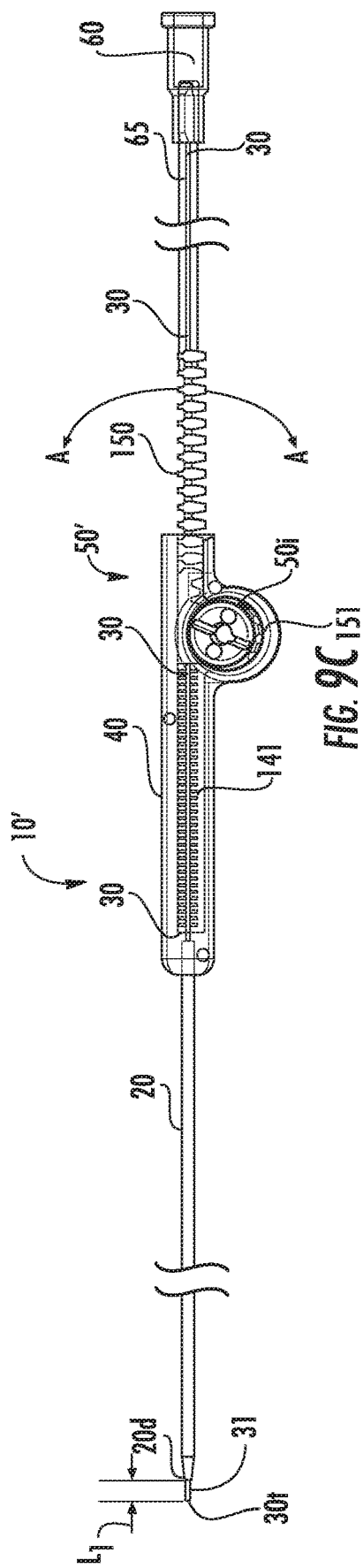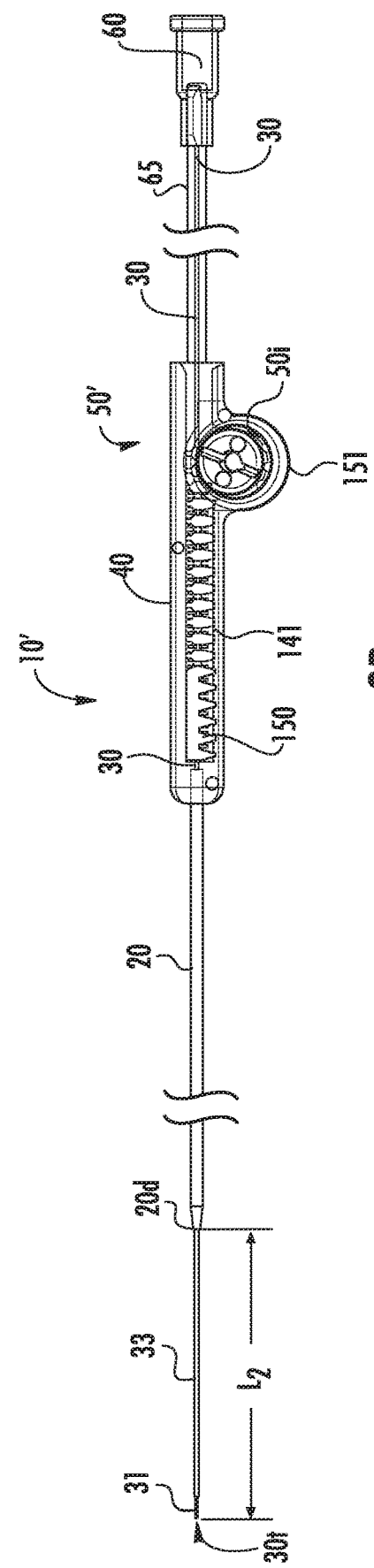

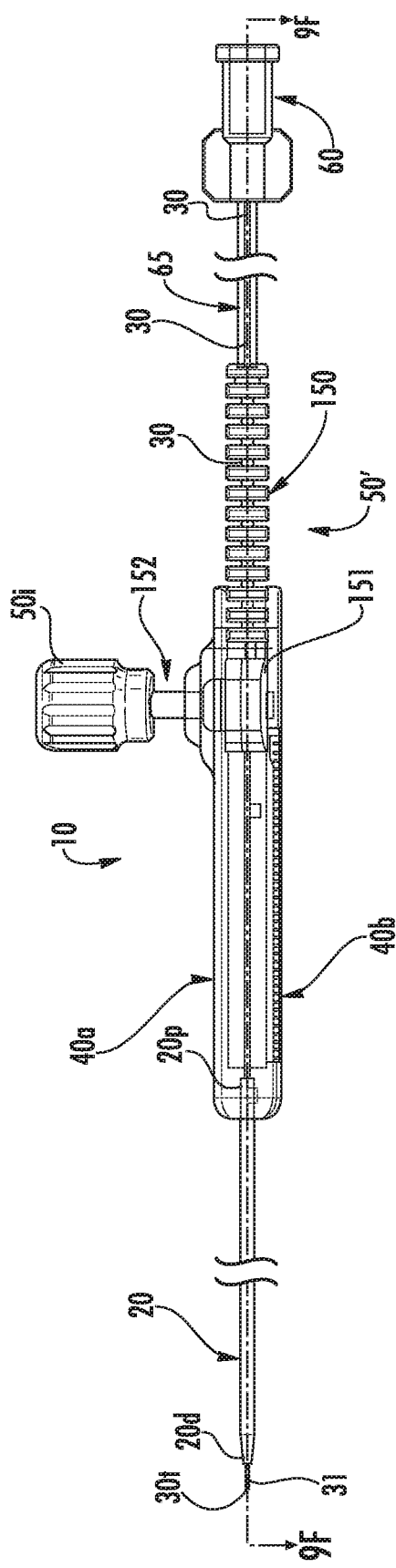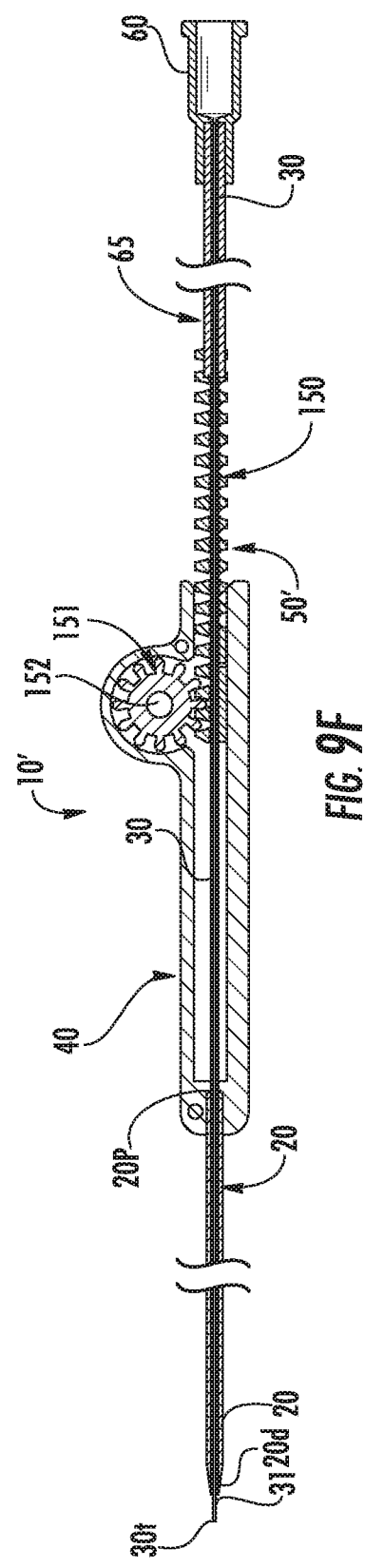
FIG. 9E
FIG. 9F

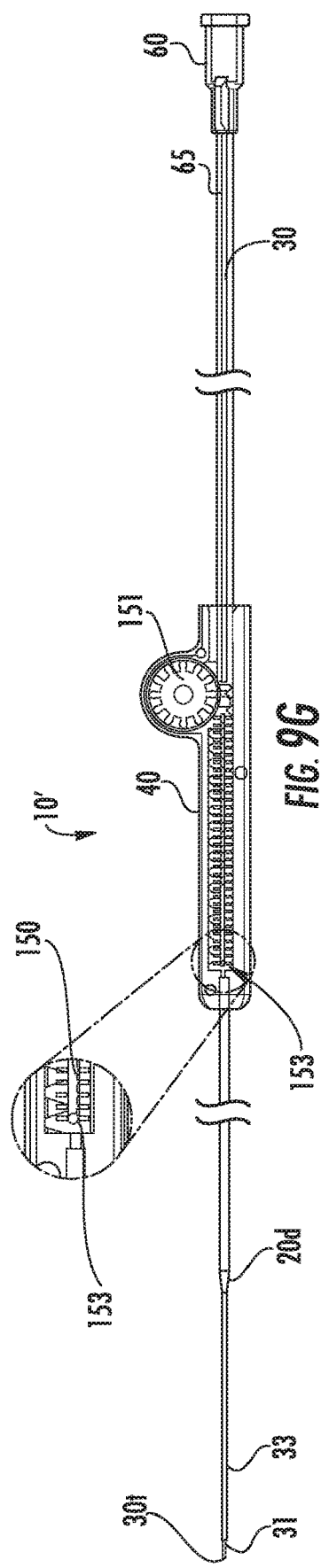
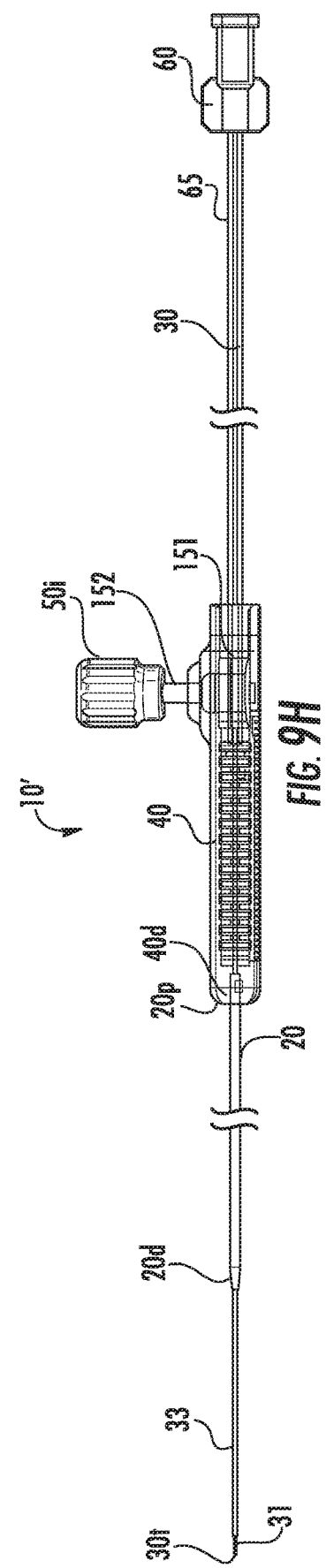

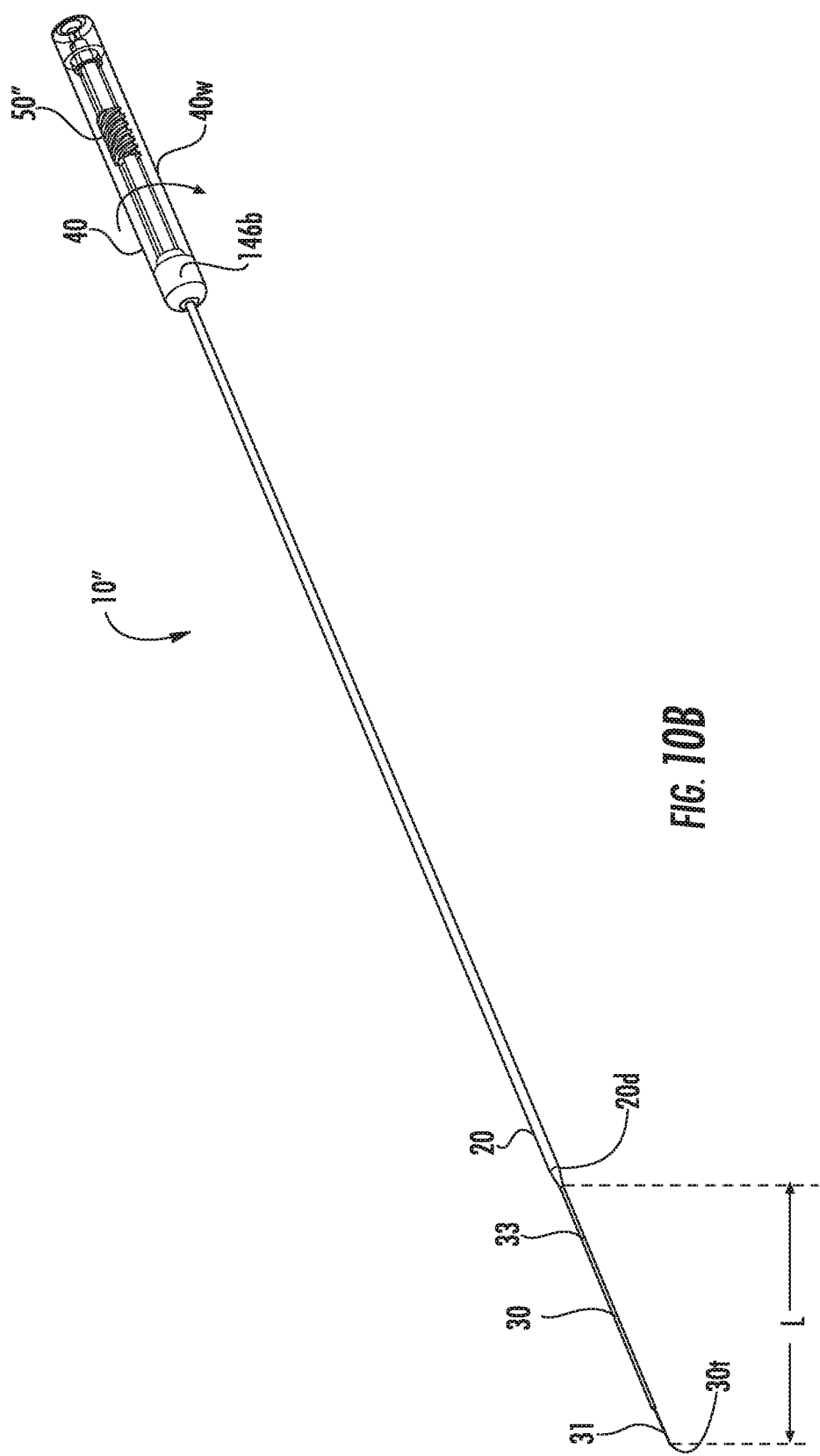

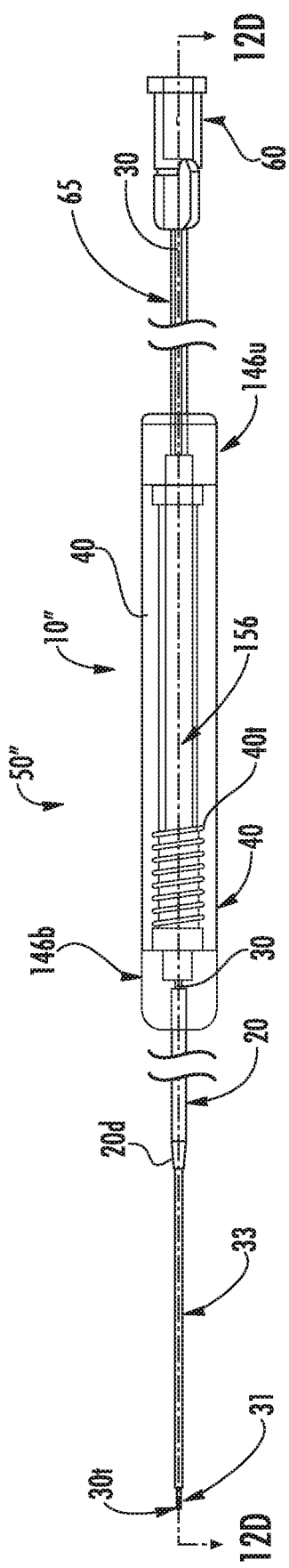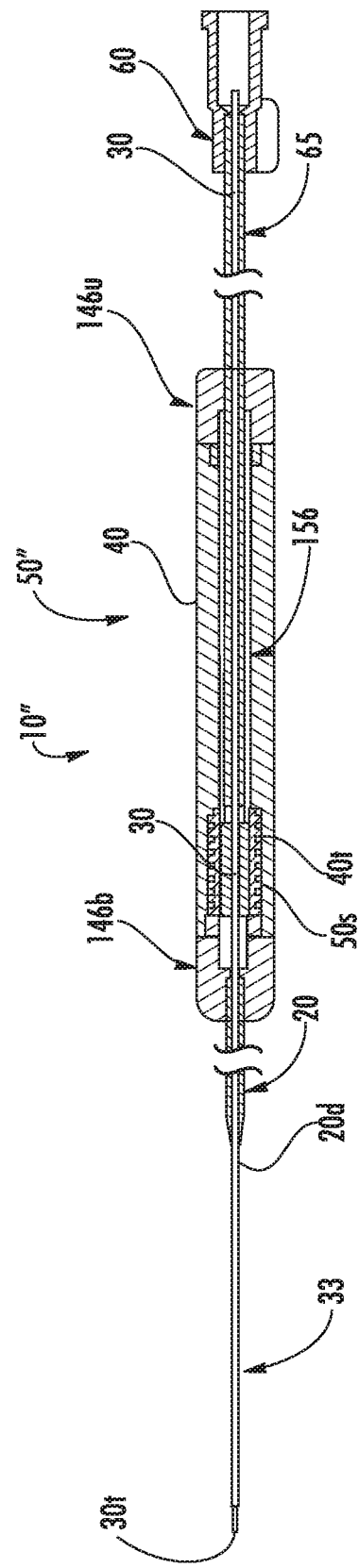
FIG. 12C
FIG. 12D

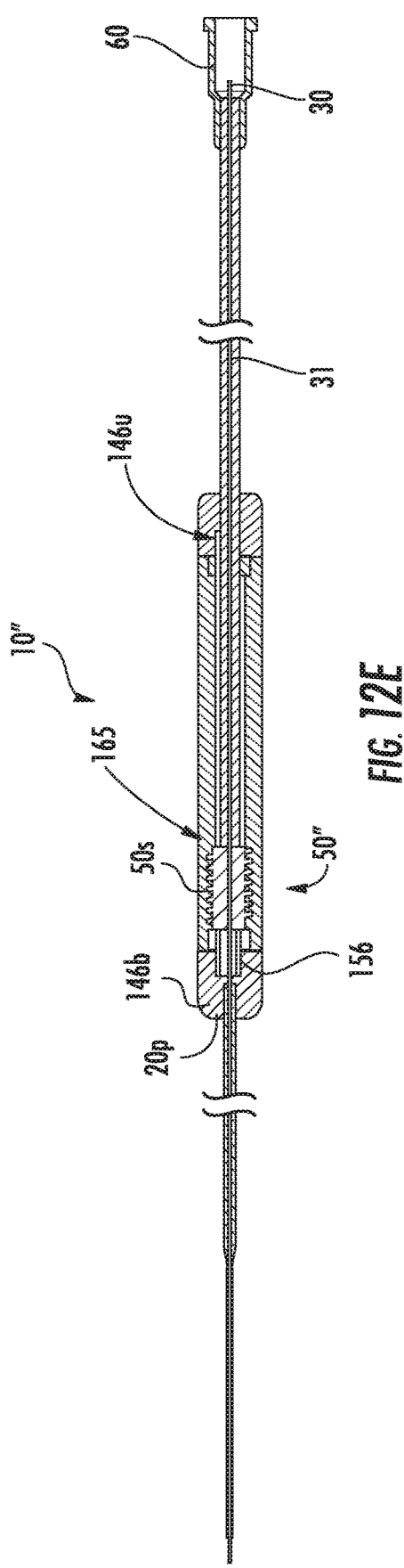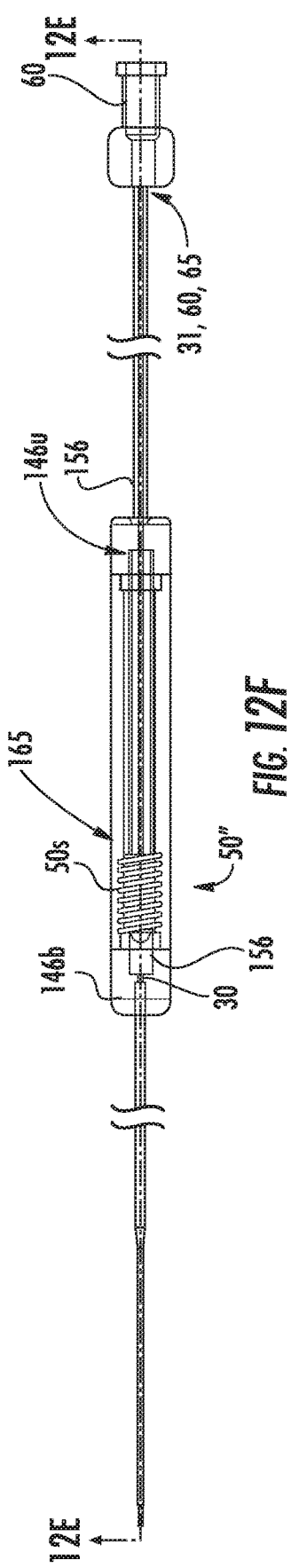

INTRABODY SURGICAL FLUID TRANSFER ASSEMBLIES WITH ADJUSTABLE EXPOSED CANNULA TO NEEDLE TIP LENGTH, RELATED SYSTEMS AND METHODS

RELATED APPLICATIONS

This application claims the benefit of and priority to U.S. Provisional Application Ser. No. 62/296,323, filed Feb. 17, 2016, and U.S. Provisional Application Ser. No. 62/382,434, filed Sep. 1, 2016, the contents of which are hereby incorporated by reference as if recited in entirety herein.

FIELD OF THE INVENTION

The present invention relates generally to medical devices and systems and, more particularly, to devices and systems for delivering and/or withdrawing substances in vivo.

BACKGROUND

Various therapeutic and diagnostic procedures require that a substance be delivered (e.g., infused) into a prescribed region of a patient, such as to an intrabody target using a delivery device. It may be important or critical that the substance be delivered with accuracy to the target region in the patient and without undue trauma to the patient.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention are directed to intrabody fluid transfer assemblies with adjustable exposed tubular cannula to needle tip length, related systems and methods.

Embodiments of the invention are directed to a surgical device for transferring fluid to or from a subject. The device includes a tubular cannula (which may be referred to as an elongate guide cannula) having opposing proximal and distal ends with an open axially extending lumen. The device also includes an elongate needle (which can also be referred to as a "capillary" or "capillary tube") having opposing proximal and distal ends. The elongate needle is configured to extend through (typically slidably insertable into) the tubular cannula lumen so that the distal end of the needle extends a distance out of the distal end of the tubular cannula. The device also includes a length adjustment housing for positional adjustment of length between the distal end of the tubular cannula and the exposed tip of the needle.

The tubular cannula and/or needle can be held in the housing to be retracted and extended from the housing.

The length adjustment housing can reside external of a patient when the distal end portion of the tubular cannula and needle are in the patient.

The housing can rotate in a defined direction to extend at least one of the needle or the cannula.

A portion of the needle resides in and/or is attached to or attachable to a length of flexible tubing. The elongate needle can be formed of fused silica glass. The distal end of the needle can have a stepped configuration with a first segment having a first outer diameter that merges into a second end segment having a second smaller outer diameter, the second segment having a length that extends to a tip of the needle.

The needle may comprise an inner capillary member and an outer capillary member of a larger diameter than the inner capillary tube but a smaller diameter than the cannula tube.

The outer capillary tube can comprise a shrink fit sleeve to sealably engage the inner wall of the lumen of the tubular cannula.

The distance that the needle tip extends out of the distal end of the tubular cannula is between about 2 mm to about 30 mm and this length can be extended or retracted relative to the tubular cannula when the tubular cannula and needle tip are in the body of a patient (i.e., a brain).

The tubular cannula can be formed of and/or include a ceramic material.

The tubular cannula can have an outer polymeric coating and/or sleeve.

The distal end of the tubular cannula can be tapered so that it has a smaller outer diameter at a tip relative to an outer diameter of the tubular cannula more proximal or rearward of the tapered distal end.

The elongate needle can be an infusate needle that has a stepped distal end configuration and is integrally attached to the flexible tubing as a subassembly.

The needle and tubular cannula can be MRI compatible for use in an MRI guided procedure.

The intrabody devices can be particularly suitable for withdrawing/introducing fluid from/into the ventricular brain.

The tubular cannula can be formed of or include a ceramic material.

The tubular cannula can have an outer polymeric coating and/or sleeve.

The distal end of the tubular cannula can be tapered so that it has a smaller outer diameter at a tip relative to an outer diameter of the tubular cannula at a more medial or proximal portion and/or rearward of the tapered distal end.

The tubular cannula can be formed of and/or include a ceramic material.

The tubular cannula and the outer capillary can each comprise a conformal outer polymeric sleeve.

The distal end portion of the needle that extends out of the tubular cannula can have at least first and second co-axially disposed segments having different outer diameters, with a smallest sized outer diameter of the first segment extending to a tip thereof.

The tubular cannula can have an exterior surface on a distal end portion thereof that tapers down in size to a tip thereof to define a third coaxially disposed stepped segment that resides a distance rearward of the second segment and has a larger outer diameter than both the first and second co-axially disposed segments.

The needle can have a fused glass silica body.

An outer surface of the tubular cannula can have a size and geometry adapted for use with a stereotactic frame.

The needle can have an inner diameter of between about 100 μm to about 750 μm.

The first smallest outer diameter segment can have a longitudinal length of between about 1 mm to about 10 mm. The second segment can have a longitudinal length of between about 2 mm to about 20 mm. The distal tip of the guide cannula can reside a distance between 3 mm to about 30 mm from a distal tip of the needle.

Yet other embodiments are directed to methods of transferring a substance to and/or from a patient, the methods include: providing a tubular cannula with an axially extending interior lumen and a needle having an internal lumen with a distal end of the needle extending out of the tubular cannula at a target site; then transferring the substance to or from the target site through the needle lumen.

The needle can be an infusion needle. The transferring the substance to or from the target site can be carried out by infusing a substance into target tissue such as into the brain or into the heart, for example.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 1A is a side view of an exemplary intrabody fluid transfer assembly shown in an exemplary first position according to embodiments of the present invention.

FIG. 1B is a side view of the exemplary intrabody fluid transfer assembly shown in an exemplary second position, with the needle tip further away from a distal end of the tubular cannula than in the first position, according to embodiments of the present invention.

FIG. 2A is a side view of the assembly shown in FIG. 1A in the first position.

FIG. 2B is a section view taken along lines 2B-2B in FIG. 2A according to embodiments of the present invention.

FIG. 3A is a side view of the assembly shown in FIG. 1B in the second position.

FIG. 3B is a section view taken along lines 3B-3B in FIG. 3A according to embodiments of the present invention.

FIG. 4A is a side view of some components of the assembly shown in FIG. 1B.

FIG. 4B is a partial exploded view of the components shown in FIG. 4A according to embodiments of the present invention.

FIG. 5A is a side view of the assembly shown in FIG. 1B in the second position according to embodiments of the present invention.

FIG. 5B is a section view taken along lines 5B-5B in FIG. 5A of the assembly shown in FIG. 5A.

FIG. 5C is a section view taken along lines 5C-5C in FIG. 5A.

FIG. 6 is an enlarged section view of components of the assembly shown in FIG. 5A according to some embodiments of the present invention.

FIG. 9C is a side partially exposed view of the infusion assembly shown in FIG. 9B illustrating a needle tip to tubular cannula retracted configuration with the gear outside the housing according to embodiments of the present invention.

FIG. 9D is a side partially exposed view of the infusion assembly shown in FIG. 9C illustrating a needle tip to tubular cannula extended configuration with the gear inside the housing according to embodiments of the present invention.

FIG. 9E is a top view with the housing shown partially transparent of the transfer assembly shown in FIG. 9C.

FIG. 9F is a section view taken along line 9F-9F in FIG. 9E.

FIGS. 9G, 9H and 9I illustrate exemplary attachment regions of various components of the fluid transfer assembly shown in FIGS. 9D and 9E according to embodiments of the present invention.

FIG. 10B is a side perspective view of the assembly shown in FIG. 10A but illustrating the exposed needle tip further extended according to embodiments of the present invention.

FIG. 11A is a side perspective, partially exploded view of the intrabody fluid transfer assembly shown in FIG. 10A.

FIG. 12C is a top view with the housing shown partially transparent of the transfer assembly shown in FIG. 9C.

FIG. 12D is a section view taken along line 12D-12D in FIG. 12C.

FIGS. 12E and 12F illustrate exemplary attachment regions of various components of the fluid transfer assembly shown in FIGS. 12A-12D according to embodiments of the present invention.

DETAILED DESCRIPTION

Figure 7:
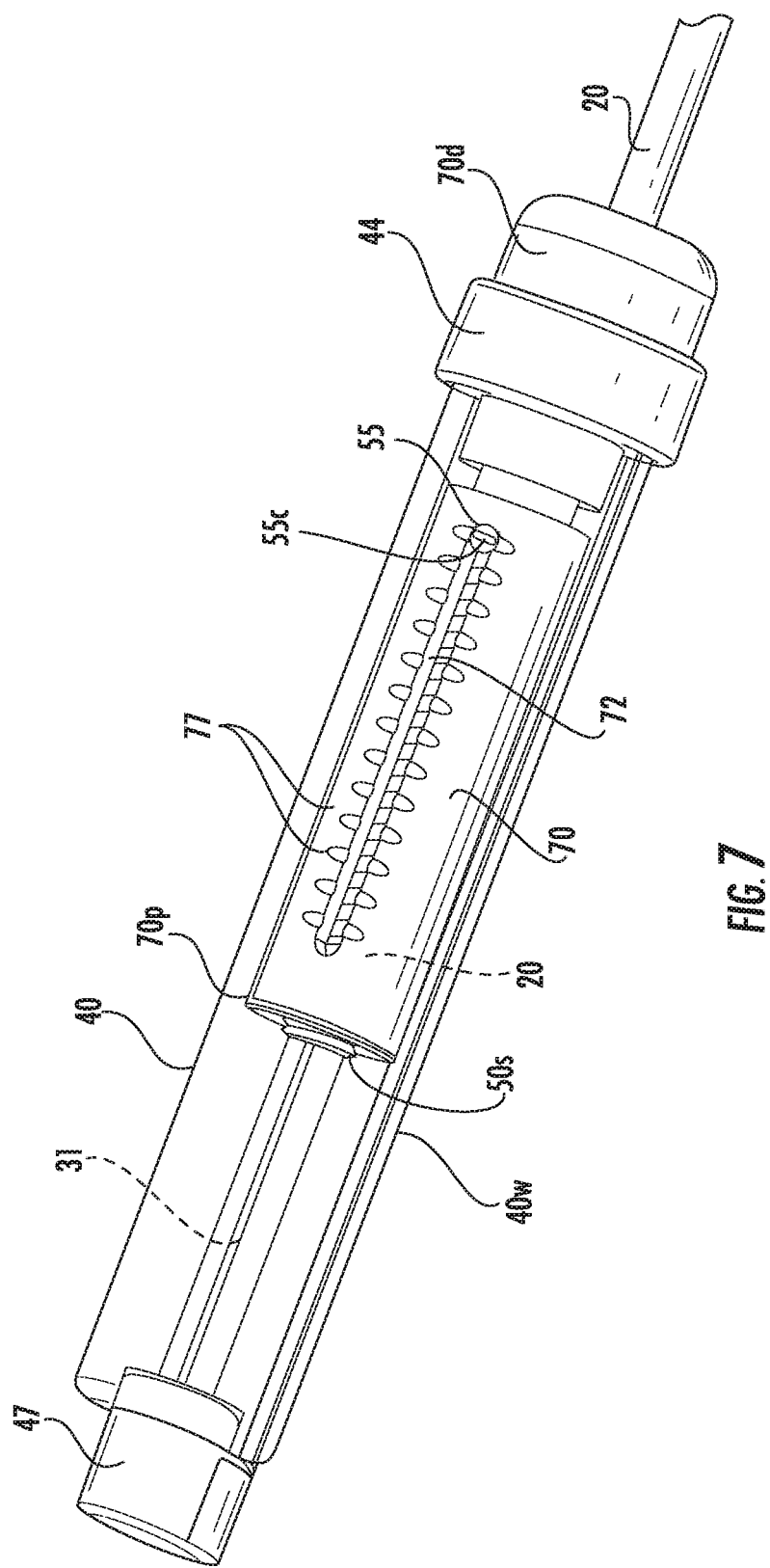
FIG. 7 is a greatly enlarged side perspective view of a housing of an assembly with a length adjustment mechanism/mechanism according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The terms "FIG." and "Fig." are used interchangeably with the word "Figure" in the specification and/or figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/−twenty percent (20%).

The term "monolithic" means that the component (e.g., needle) is formed of a single uniform material.

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5T (Tesla), typically above 1.0T, and more typically between about 1.5T and 10T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near "real-time" imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "sterile," as used herein, means that a device, kit, and/or packaging meets or exceeds medical/surgical cleanliness guidelines, and typically is free from live bacteria or other microorganisms.

Embodiments of the present invention can be utilized with various diagnostic or interventional devices and/or therapies to any desired internal region of an object using any suitable imaging modality, typically an MRI and/or in an MRI scanner or MRI interventional suite. However, CT or other imaging modalities may be used. The object can be any object, and may be particularly suitable for animal and/or human subjects for e.g., animal studies and/or veterinarian or human treatments. Some embodiments deliver therapies to the spine. Some embodiments deliver therapies to treat or stimulate a desired region of the sympathetic nerve chain.

Other uses, inside or outside the brain, nervous system or spinal cord, include stem cell placement, gene therapy or drug delivery for treating physiological conditions, chemotherapy, drugs including replicating therapy drugs. Some embodiments can be used to treat tumors.

The term "substance," as used herein, refers to a liquid for treating or facilitating diagnosis of a condition and can include bions, stem cells or other target cells to site-specific regions in the body, such as neurological, nerves or other target sites and the like. In some embodiments, stem cells and/or other rebuilding cells or products can be delivered into spine, brain or cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The term "infusion" and derivatives thereof refers to the delivery of a substance (which can be a single substance or a mixture) at a relatively slow rate so that the substance can infuse about a target region. Thus, the term "infusate" refers to a substance so delivered.

Embodiments of the present invention will now be described in further detail below with reference to the figures. FIGS. 1A and 1B illustrate an exemplary intrabody fluid transfer assembly 10 with a tubular cannula 20, a needle 30 and a housing 40 with a length adjustment mechanism 50 attached (directly or indirectly) to one or both of the tubular cannula 20 and needle 30 to be able to extend and retract one or both relative to the distal end 40d of the housing. The term "needle" refers to a relatively small device with an open lumen (30l, FIG. 5C) extending to its tip 30t to release or intake fluid.

The tubular cannula 20 can comprise a different material than the needle 30. Where the needle 30 comprises inner and outer capillary tubes 31, 33, the outer capillary tube 33 can be shorter than the inner capillary tube 31 and may terminate inside the housing 40. By way of example only, the tubular cannula 20 can be a ceramic tube that has increased rigidity relative to the needle and the needle 30 can be formed of fused silica.

The length adjustment mechanism 50 is configured to adjust a distance or length $D_1$ between the distal end 20d of the tubular cannula and the exposed tip 30t of the needle. The length adjustment mechanism 50 can be configured to provide a maximal stroke length of between 0.5 inches and 3 inches, more typically between about 0.75 inches to about 1 inch (2.5 cm) such as about 0.79 inches. The length adjustment can be carried out in vivo while the housing remains external of a patient with the distal end of the cannula 20d and needle tip 30t in the body of the patient.

The distal end of the housing 40d can reside at a distance that is between 4-10 inches from the needle tip 30t, more typically between 4 and 5 inches. This length can remain fixed in some embodiments.

The needle 30 may comprise an inner capillary tube 31 with a length sufficient to define the tip 30t and may have an outer capillary tube 33 that resides a distance rearward from the tip 30t to form at least one stepped distal end portion 30s (so that the needle 30 merges from a larger diameter to a smaller diameter at a distal end portion thereof, toward the tip 30t) of the needle 30. This stepped portion can define a surface that is orthogonal to the cannula/needle axis.

As shown in FIGS. 1A and 1B, the tubular cannula 20 can have opposing proximal and distal ends 20p, 20d, respectively. The tubular cannula 20 can have an external exposed stepped and/or tapered segment 21 (the outer diameter becoming smaller in a direction of the needle tip 30t). The distance between the distal end of the tubular cannula 20d and the needle tip 30t can be adjusted by a user to position the tapered segment 21 closer or further away from the needle tip 30t.

As shown in FIGS. 1A, 2A and 2B, for example, in a first configuration, the needle tip 30t resides at a short distance "$D_1$" from the distal end of the cannula 20d while in FIG. 1B, in a second configuration, the distal end of the cannula 20d resides at a longer distance $D_2$ from the needle tip 30t. $D_2$ can be between about 0.5 inches and about 3 inches, more typically between about 0.5 inches and about 1.1 inch. $D_1$ can be between about 1 mm to about 50 mm, typically between 1 mm and 10 mm, and in some embodiments between about 2 mm to about 4 mm, such as about 3 mm.

The needle tip 30t may be configured to reside at a fixed extended length from the distal end 20d of the housing which may be between about 4 and 6 inches, more typically between about 4.8 and about 5 inches, in some particular embodiments.

In some particular embodiments, the distal end of the tubular cannula 20d can reside at a length $L_2$ that is about 4.7 inches in a fully extended position (FIG. 1A) and at about 3.93 inches in a fully retracted position (FIG. 1B). However, other stroke distances and extended and retracted lengths may be used.

Referring to FIG. 1B, the distal end portion of the needle 30d can have at least one stepped segment 30s that can have an increased outer diameter relative to the tip 30t. The stepped segment 30s can reside in the distal end of the cannula 20d in the configuration shown in FIGS. 1A, 2A and 2B.

The stepped segment 30s can reside a fixed length D1 from the tip 30t. $D_1$ can be, for example, between about 1 mm to about 50 mm, typically between 1 mm and 10 mm, and in some embodiments between about 2 mm to about 4 mm, such as about 3 mm. In the configuration shown in FIG. 1B, for example, the needle 30 can have an exposed length $L_3$ that extends rearward from the stepped segment 30s with the increased outer diameter out of the distal end of the tubular cannula 20d. $L_3$ can be longer than $D_1$ and can be between about 2 mm and 20 mm. The distal end portion of the needle 30d may include more than two co-axially aligned (concentric) stepped segments 30s.

The tubular cannula 20 can have a length $L_2$ that extends out of the housing 40 that varies to provide the positional adjustment relative to the tip. In other embodiments, the tubular cannula 20 can remain fixed in position in the housing 40 and the needle 30 can be extended and retracted relative to the housing 40. In yet other embodiments, the tubular cannula 20 and the needle 30 can each be extendable and retractable out of the distal end of the housing 40d.

The length $D_2$ of the distal end portion of the needle 30 outside the cannula 20 during delivery can be between about 3 mm to 30 mm. These lengths can be selected to inhibit reflux and/or provide a desired delivery path during infusion.

The needle 30 can have a stepped distal end portion that cooperates with the cannula 20 to form co-axially disposed step segments (the orthogonally extending end face at the distal end 20d of the cannula, and the stepped segment 30s of the needle. There can be three different outer diameters that are longitudinally separated with steps on one or more of end faces $S_1$, $S_2$, $S_3$ (FIG. 4A). One or some of the steps $S_1$, $S_2$, $S_3$ can serve to reduce or prevent reflux of the delivered substance. The end face at taper segment $S_3$ can be a conical face rather than an orthogonal end face provided at $S_1$ and $S_2$ (orthogonal to the axial direction of the needle axial direction and the tubular cannula axial direction).

According to some embodiments, the inner diameter of the needle 30 is in the range of from about 10 μm to 1 mm and, in some particular embodiments, is between about 100 μm to about 750 μm, such as about 200 μm. According to some embodiments, the outer diameter at the tip 30t is in the range of from about 75 μm to 1.08 mm and, in some embodiments, is about 360 μm.

In some embodiments, as shown in FIGS. 1A and 1B, for example, an outer wall 40w of the housing 40 can be (manually or electro-mechanically) rotated in a first direction (indicated by the arrow with the letter "R") to retract the length adjustment mechanism 50 in the housing 40, which, in turn, exposes a larger length of the distal end of the needle 30 (FIGS. 1B, 3A, 3B). The rotation can be in either direction for the retraction and is typically manually carried out. The rotation of the outer wall of the housing 40w can retract the tubular cannula 20 and/or extend the needle 30.

The rotatable outer wall 40w can be the entire outer wall or a portion of the outerwall. The rotatable outer wall 40w can be between about 1 about 6 inches long and may have a small diameter, greater than the diameter of the outer wall of the tubular cannula 20 and less than about 0.3 inches, in some embodiments. The rotatable outer wall 40w can be cylindrical.

According to some embodiments, at least part of an exposed length of the tubular cannula 20 has an outer surface comprising a polymeric support sleeve 23 (FIG. 3A) which can comprise a shrink tube and may have a thickness in the range of from about 40 μm to about 60 μm.

While different sizes may be appropriate for different uses, the tubular cannula 20 can, in some embodiments, have an outer diameter that is between about 0.2 inches and 0.015 inches, such as, in some particular embodiments about 0.061 inches and an inner diameter that is between 0.10 inches and 0.001 inches, such as, in some particular embodiments, about 0.029 inches. The tubular cannula 20 can have a lower portion with a smaller outer diameter than an upper or proximal portion or may have a constant outer diameter over its length to the tapered segment 21.

The needle 30 can be fused silica and may also include an outer wall covered by a sleeve 35 which can comprise a shrink tube or other polymeric sleeve or coating, typically starting at the stepped segment 30s and extending a length over the outer capillary 33 as shown, for example in FIGS. 3A and 5C, to facilitate a suitably fluid-tight interface at the distal end of the tubular guide cannula 20d to inhibit or reduce fluid entry into this interface/space during delivery or intake. The sleeve 35 can be polyester and can have a thickness that is between about 0.00125 inches and 0.00150 inches (0.032-0.038 mm), in some embodiments.

As shown in FIGS. 1A, 1B, 2A and 2B, for example, the assembly 10 can have a connector 60, such as a female or male luer connector (shown as female) that resides a distance away from the housing 40, typically a length that positions an upper/outer end 60e a distance between 3-20 inches away from the proximal end of the housing 40p, more typically between about 6-10 inches. The needle 30 (typically only the inner capillary 31 without the outer capillary 33, where used) can extend through the housing 40 to an internal portion of the connector 60 to be in fluid communication with the connector 60. Tubing 65, such as PVC tubing, can extend between a proximal end of the housing 40p to the connector 60 about the needle 30. The needle 30 can have a total length between the connector 60 and tip 30t that can be at between about 10-20 inches, typically about 15.65 inches.

Referring to FIGS. 3A, 3B, 4A and 4B, in some embodiments, the length adjustment mechanism 50 can comprise a longitudinally extending screw 50s that resides in the housing 40 and that can controllably translate in an axial direction to provide the positional adjustment of the distance between the distal end of the tubular cannula 20d and the needle tip 30t. However, it is contemplated that other length adjustment mechanisms may be used, such as, for example, gears such as worm gears, planetary gears, rack and pinions and the like, cams, ratchets, frictional slides, and/or linkages.

The housing 40 can include an internal, longitudinally extending threaded segment 40t that engages threads 50t of the length adjustment screw member 50s. Thus, the outer wall of the housing 40w can rotate and act as a nut to be able to threadably engage and rotate the screw 50s. The screw 50s can have a relatively fine pitch configuration, such as a thread configuration of 3-48 (48 threads per inch). The screw 50s can be of brass for MRI compatibility, but other materials may be used as well as other pitch configurations.

In the embodiment shown in FIGS. 2B, 3A and 3B, for example, an outer wall 20w of the tubular cannula can be fixably attached to the screw 50s, typically bonded, so that the threads form the outerwall of a portion of the tubular cannula 20w (typically a proximal end portion of the cannula 20p) but other fixation configurations may be used.

In some embodiments, the outerwall of the tubular cannula 20w can have the thread pattern formed directly therein. In some embodiments, the needle 30 can be fixably attached to the screw 50s (not shown) to allow length adjustment. In some embodiments, more than one internal screw can be used, one attached to the tubular cannula 20 and one attached to the needle 30 and separate portions of the housing 40 or members held by the housing 40 can be used to selectively move each of the cannula 20 and the needle 30 to provide adjustable exposed lengths (not shown).

Referring to FIGS. 2B, 3B, 4A and 4B, the housing 40 can have an axially extending lumen 41 and an inner, longitudinally extending wall or surface 41s extending about the lumen, at least a longitudinally extending segment of which can be threaded 40t, typically for a sub-length of the overall length of the housing 40 residing between the proximal and distal ends of the housing. The threads 40t can be configured to define hard stops at fully retracted and fully extended positions which can be associated with a short linear distance of between about 0.5 inches and 1.25 inches.

The housing 40 can be manually held by a finger(s) or hand of a user during use to allow for manual rotation of the housing outer wall 40w or other user input to the screw 50s or may be supported by a support frame or member (not shown).

The device 10 may also include a handle body 70 held in the housing 40 that has a longitudinally extending slot 72 that allows a laterally extending pin 55 attached to the screw 50s and/or tubular cannula 20 in the embodiment shown, to move therein. The handle body 70 and/or outer surface of the housing 40 thereat can include visual indicia of position 77 such as symmetrically spaced apart marks and/or a graduated scale, for example. The pin 55 can include a color-contrast segment 55c (FIG. 7) that extends across the slot 72 at or above an outer surface of a wall at the slot 72 to align with aligned spaced apart visual indicia marks 77 across the slot to facilitate visual recognition of the extended or retracted length position (distance between the needle tip 30t and distal end of the guide cannula 20d).

The handle body 70 can have an elongate cylindrical shape with an axially extending interior cavity surrounding the tubular cannula 20 and may be encased in the housing 40. The housing 40 can have a transparent or visually transmissive outer wall 40w. The handle body 70 can have a proximal end 70p that resides in the housing 40, typically abutting a ledge forming a pocket 40k (FIGS. 2B, 3B) and a larger distal end 70d that defines the distal end of the housing 40d allowing the tubular cannula 20 to extend therethrough when assembled (FIGS. 2A, 2B, 3A and 3B, for example).

In some embodiments, the handle body 70 can provide some or all of the internal threads 40t that cooperate with the screw 50s. In some embodiments, the handle body 70 is devoid of internal threads and merely allows the tubular cannula 20 and/or threaded member 50s to longitudinally (slidably) translate closely spaced thereto in the cavity of the handle body 70.

The handle body 70 can be attached to an innerwall 40i of the housing (FIGS. 2B, 3B) and/or may be held in the pocket 40k (FIG. 2B) extending between a medial to a distal end portion of the housing 40. A support member 44 can be affixed to a distal end of the housing 40d to lock the handle body 70 in position while allowing the lower end portion of the tubular cannula 20 to extend out from the housing. The handle body 70 can be static and can allow the pin 55 to move up and down along the slot 72 to inhibit rotation of the handle body 70 during rotation of the screw 50s.

A proximal support member 47 can be attached at a top of the housing 40. The proximal support member 47 can have a small rigid tubular projection that attaches to the flex tubing 65 that extends a distance such as between 1-10 inches, typically about 3-8 inches, between the support member 47 and connector 60. In other embodiments, the connector 60 can be directly attached to the end member 47 and/or housing 40 (not shown).

The support end members 44, 47 and the handle body 70 can all remain stationary during use as the outerwall 40w is rotated. The end support members 44, 47 can capture the housing 40 therebetween, which can rotate in response to a user's direction clockwise and or counterclockwise to cause the translation and adjust the needle tip 30t to the distal end of the cannula 20 length. Thus, the wall of the housing 40 and the screw 50s can rotate to move the tubular cannula 20 (as shown) and/or the needle 30 (not shown).

The outer wall of the housing 40w can include an elongate bracket 42 (FIGS. 2B, 4B) that is adjacent but laterally spaced apart from the rotatable outer wall 40w and can be attached to each end member 44, 47.

Referring now to FIGS. 3A, 3B, 5A, 5B, 5C and 6, for example, and in some exemplary embodiments, the needle 30 can comprise the inner capillary tube 31 and the outer capillary tube 33 and the tubes 31, 33 can be fixably attached, typically bonded together, so that they have a fixed configuration relative to each other such that the inner capillary 31 extends about 3 mm from the distal end of the outer capillary 33. An external polymeric conformable tube (i.e., a polyester shrink wrap tube) 35 can reside over the outer capillary tube 33 at least for a distance that can be external of the housing and/or distal end of the cannula 20d.

The length adjustment mechanism 50 can be fixably attached (typically bonded) to the needle 30 or the tubular cannula 20. The external polymeric conformable tube (i.e., a shrink wrap tube) 23 can reside over an exposed length of the cannula 20, typically over a distal end thereof 20d with the tapered end 21. The pin 55 can also be attached (i.e., bonded) to the screw 50s and/or tubular cannula 20. The screw 50s can be affixed to a proximal end portion of the tubular cannula 20p, typically for a length between about 0.5 inches and 2 inches, more typically between about 0.75 inches and 1.1 inches, in some embodiments. The tubular cannula 20 and outer capillary 33 can terminate inside the housing 40, typically adjacent the proximal end 70p of the handle body). The upper end support 47 can be fixably attached (i.e., bonded) to the housing proximal end 40p and the support tube 65 can be affixed to the end support 47. The end support member 44 can be affixed (i.e., bonded) to the distal end portion of the handle body 70d. The support tube 65 with inner capillary tube 31 can also be fixably attached (i.e., bonded) to the connector 60.

Figure 8A:
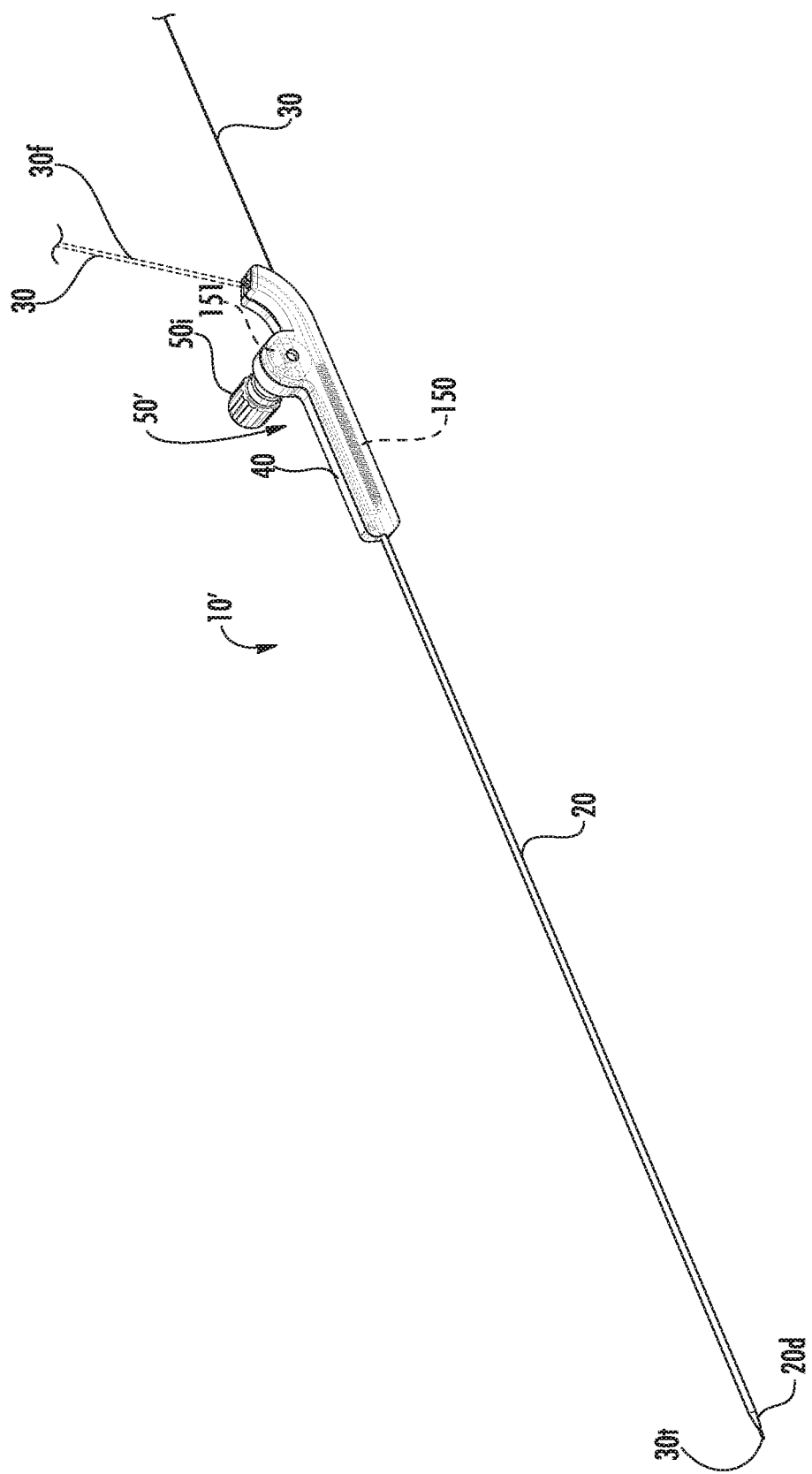
FIG. 8A is a side perspective view of another embodiment of an intrabody fluid transfer assembly according to embodiments of the present invention.
Figure 8B:
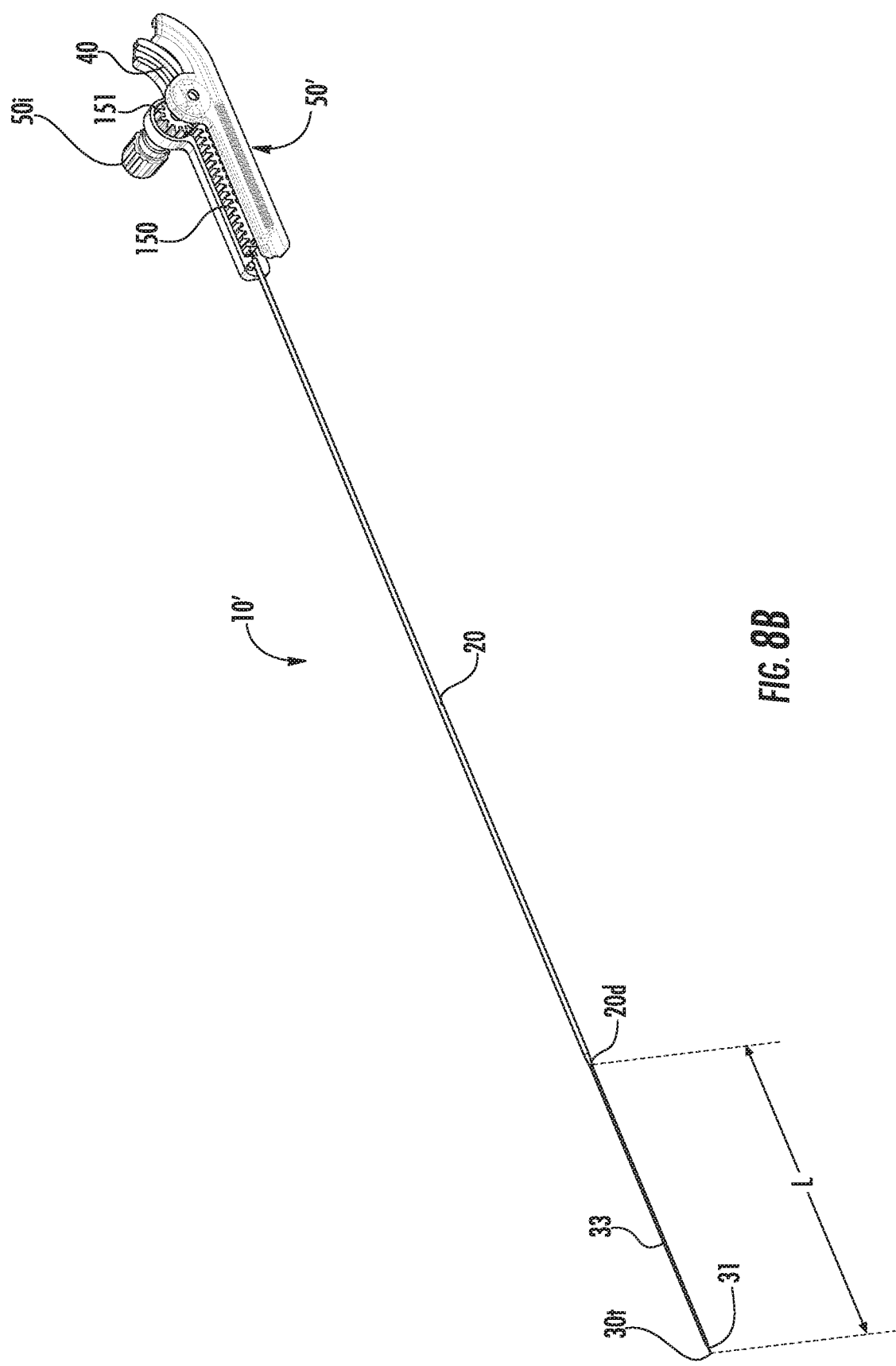
FIG. 8B is a side perspective view of the assembly shown in FIG. 8A but illustrating the exposed needle tip further extended according to embodiments of the present invention.

Referring to FIGS. 8A, 8B, 9A and 9B, the assembly 10' can have a length adjustment mechanism 50' that can include an external user interface member 50i (shown as a thumbwheel) that extends laterally outward a distance beyond the housing 40 that is attached to the housing 40. As shown, this mechanism 50' includes a pinion gear 151 that engages a longitudinally extending internal rack gear 150 inside the housing 40. FIG. 8A illustrates a retracted configuration of the needle tip 30t and FIG. 8B illustrates an exemplary extended position of the needle tip 30t relative to the distal end 20d of the tubular cannula 20. Thus, the outer wall 40w is not required to rotate. The rack gear 150 can be bonded or otherwise fixedly attached to the needle 30 (typically the inner capillary tube 31). The tubular cannula 20 can be rigid and held by a distal end 40d of the housing 40 to have a fixed length (i.e., it does not move).

Figure 9A:
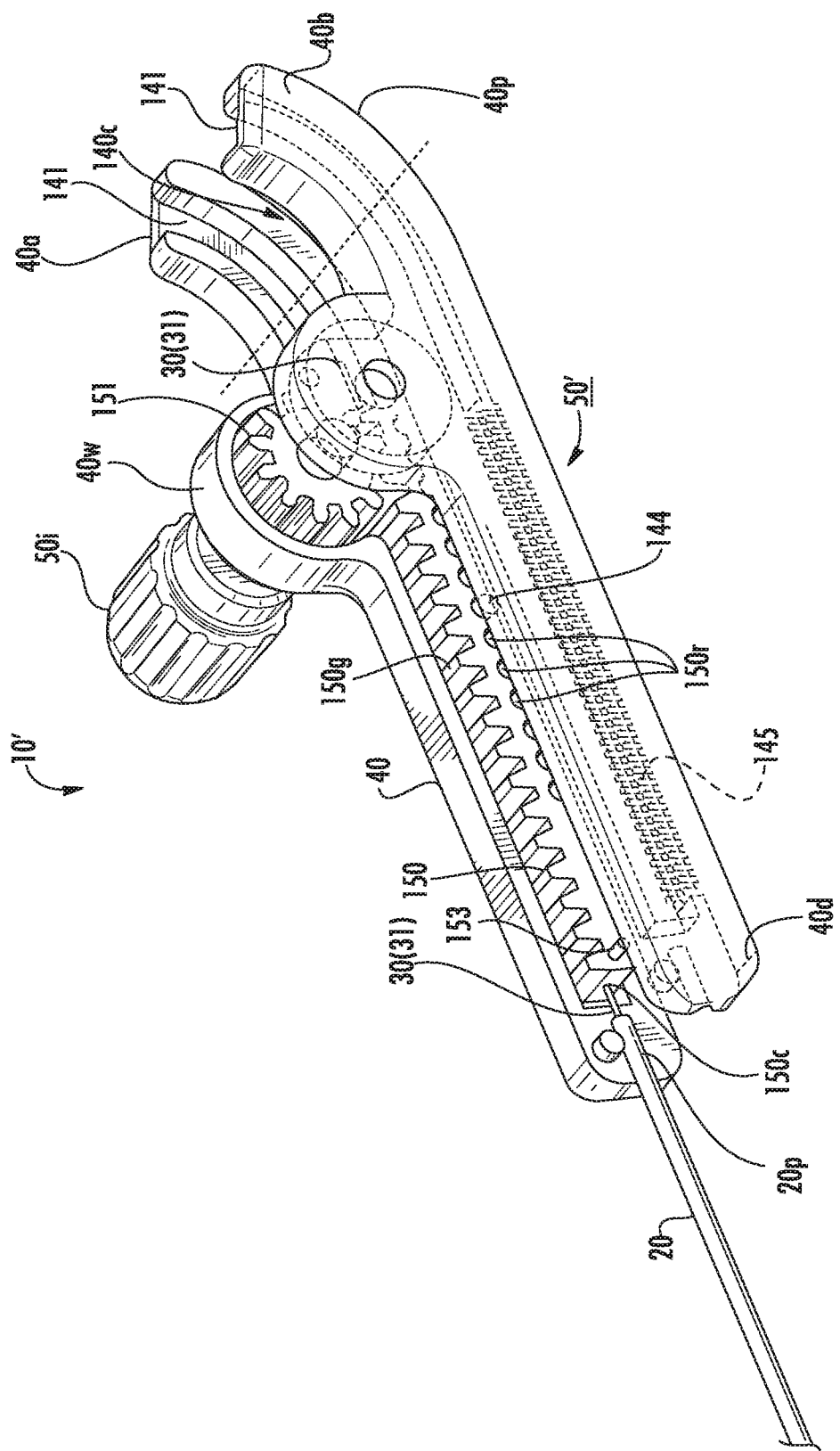
FIG. 9A is a greatly enlarged partially transparent view of the housing assembly shown in FIGS. 8A and 8B.
Figure 9B:
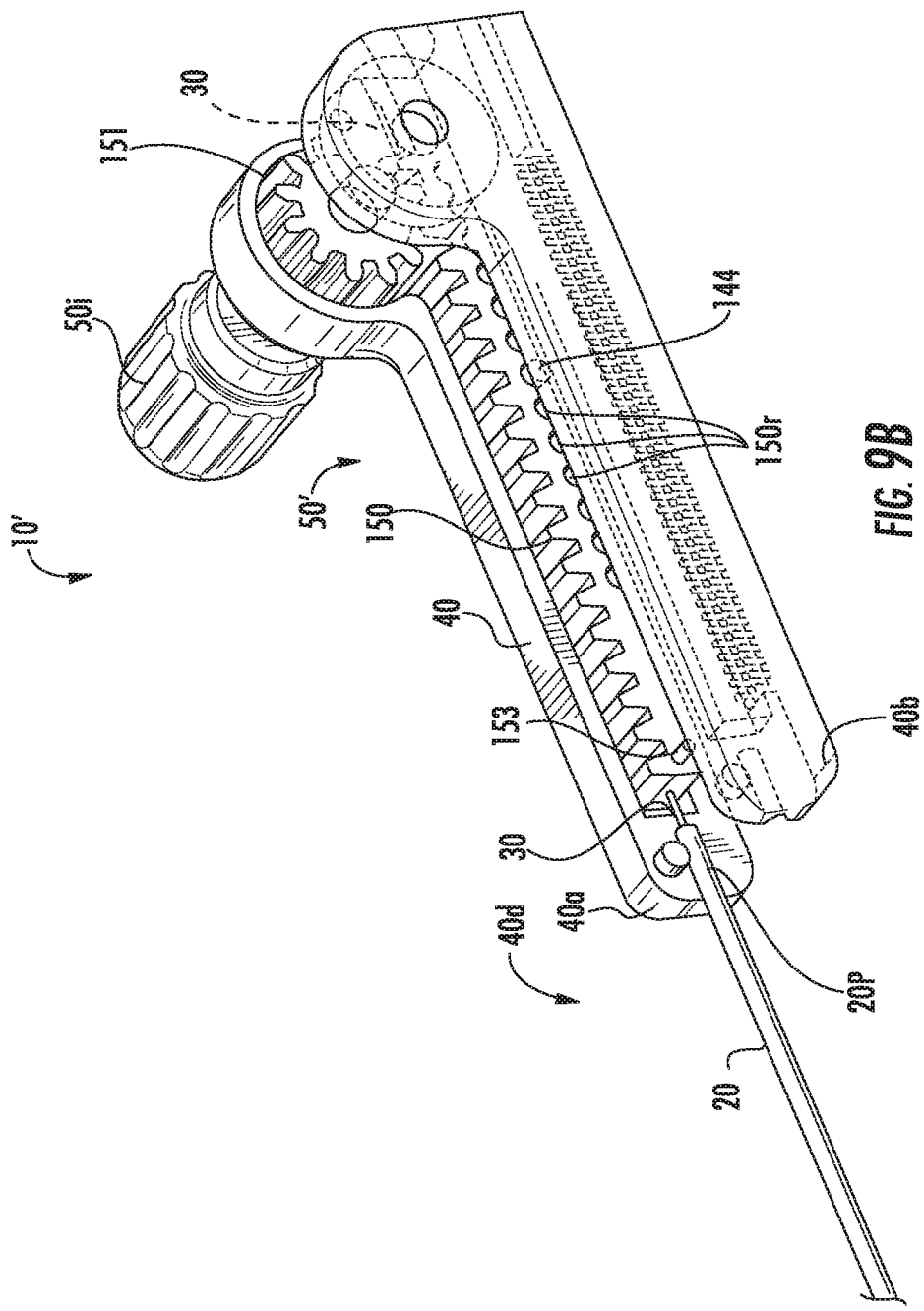
FIG. 9B is a greatly enlarged partially transparent view of another embodiment of a housing for the assembly shown in FIGS. 8A and 8B according to embodiments of the present invention.

Referring to FIGS. 9A and 9B, the rack gear 150 can have longitudinally extending gear teeth 150g on one side that face the pinion gear 151 and can have a series of longitudinally spaced apart recesses 150r (shown as arcuate recesses) along a length of the other opposing longitudinally extending side that can slidably engage a pin 144 extending laterally inside a cavity 140c provided by mating first and second housing members 40a, 40b. The housing members 40a, 40b can include a longitudinally extending slot 141 that cooperate to hold the rack gear 150 in position. The rack gear 150 can pull the needle 30 up and down relative to the housing and the tubular cannula 20 to adjust the position of the exposed needle tip 30t. The rack gear 150 can optionally include alignment tabs 153 that can engage alignment slots 145 in the inner wall of one or both of the housing members 40a, 40b.

The rack gear 150 can be flexible (meaning it can be compressed or bent side to side or front to back using a small bending force or pressure). The rack gear 150 can have sufficient rigidity to have a self-supporting three dimensional shape but can flex in any direction when outside the housing 40. FIG. 9C illustrates by the arrows above the gear with an exemplary flex axis A, that the gear 150 can bend side to side relative to the housing 40 when extended from the housing 40 with the needle 30 (typically inner capillary 31) extending out each longitudinally extending end thereof. The rack gear 150 can comprise a polymer such as a nylon or polycarbonate and may be injection molded.

As shown by the broken line extension 30f of the needle in FIG. 8A, the extension of the needle 30 can be flexible and can loop and/or bend when held loose and not supported by a support member. The pinion gear 151 may also be flexible or may comprise a different material than the rack gear and may be rigid, semi-rigid or be less flexible than the rack gear 150.

FIGS. 8A, 8B and 9A illustrate that the housing 40 can curve (be arcuate, concave or convex) typically having a straight segment that can optionally curve above the external length adjustment mechanism 50' and/or pinion gear 151. The internal slots 141 can direct the rack gear 150 to take on a conformal curved shape when it travels into this space.

FIG. 9B shows that the housing 40 can be shorter and straight, relative to the configuration shown in FIG. 9A, for example.

FIGS. 9C, 9F and 9E illustrate a needle tip 30t to distal end of tubular cannula 20 in a retracted configuration (the needle tip 30t is closer to the distal end of the tubular cannula 20 than in an extended configuration/position) with the gear 150 outside the housing 40 according to embodiments of the present invention. The gear 150 can be exposed but typically extends and retracts in adjacent tubing 240 (FIG. 13) with the inner capillary 31 and/or other needle 30 and/or capillary member. The needle 30 can travel longitudinally maximally a stroke distance between extended and retracted positions between 1-6 inches, such as between 2-4 inches, while the tubular cannula 20 is fixed in its length relative to the needle and/or housing 40.

FIG. 9D illustrates a needle tip 30t to distal end 20d of the tubular cannula in an extended configuration with the gear 150 totally inside the housing 40 and its distal end closer to the bottom member 146b than in the position shown in FIG. 9E, for example.

FIGS. 9C-9F also illustrate that the fluid transfer assembly 10' can include a tube 65 that encloses the needle 30 and that extends above the housing 40 to a connector 60, typically a luer connector as discussed above.

FIGS. 9E and 9F illustrate that the rotatable user interface member 50i can include a drive shaft 152 that is attached to a center of the pinion 151 so that rotation of the member 50i rotates the pinion 151, which moves the rack gear 150 holding the needle 30.

Figure 9I:
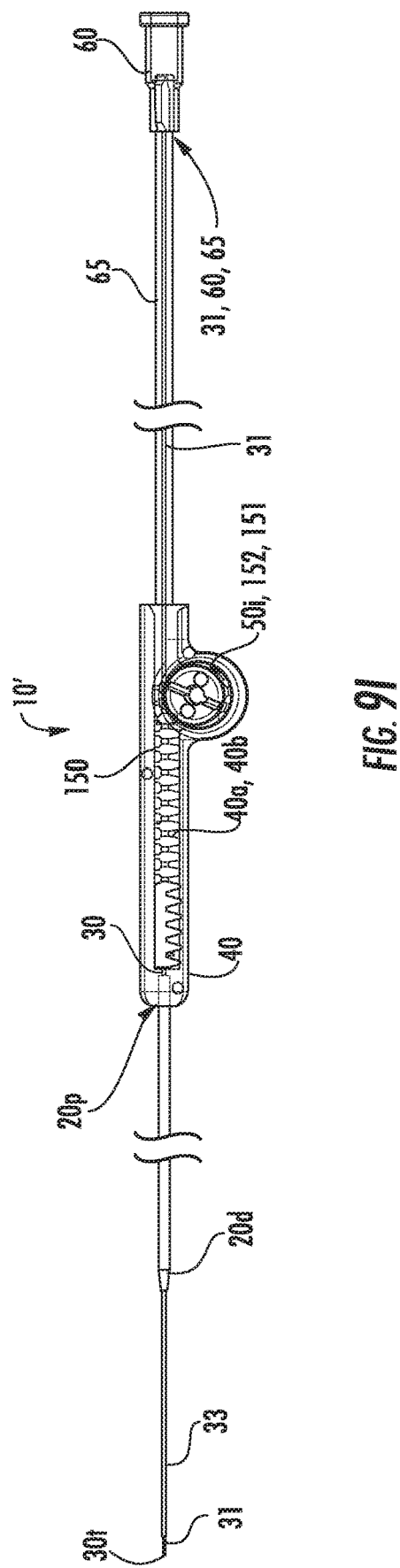
Figure 10A:
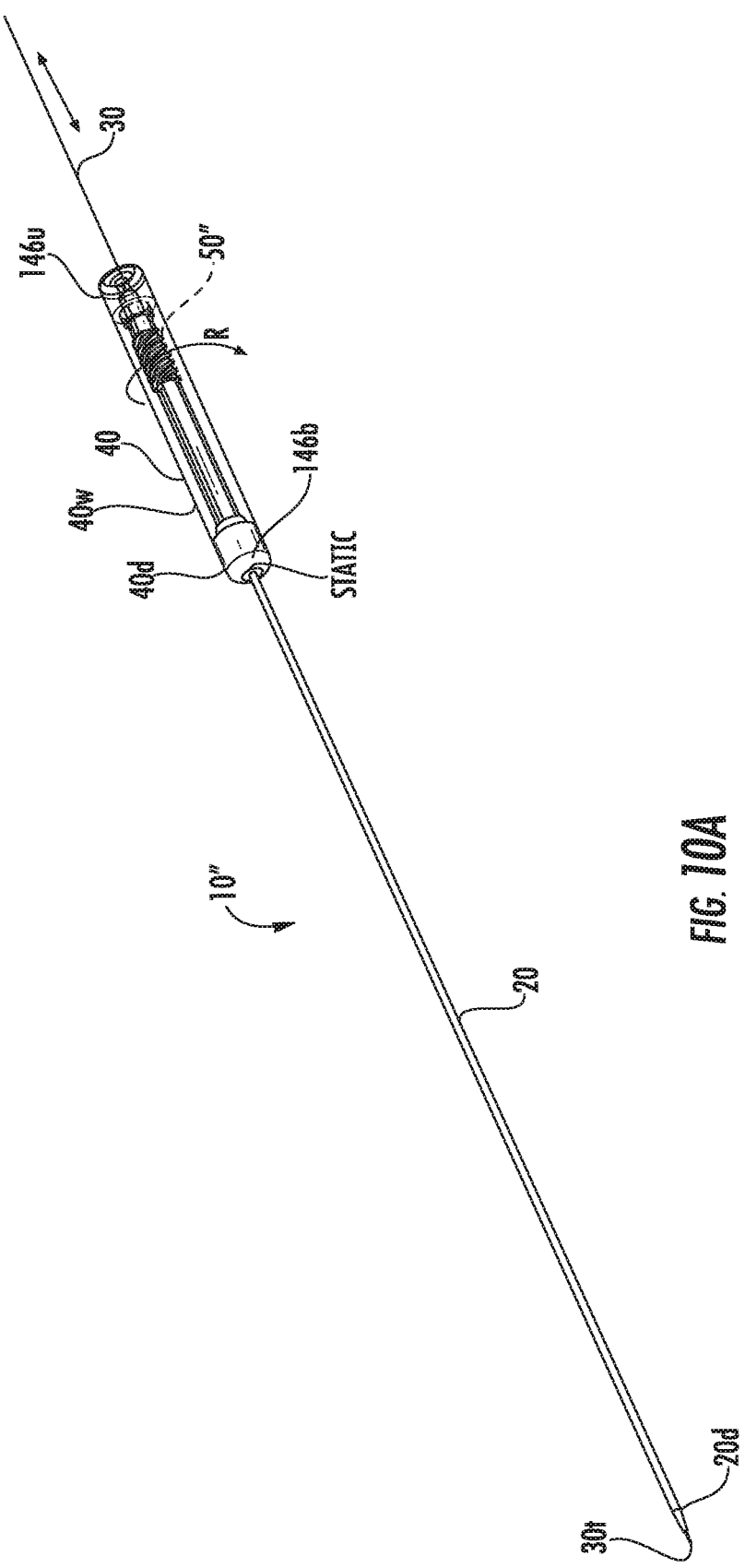
FIG. 10A is a side perspective view of another embodiment of an intrabody fluid transfer assembly according to embodiments of the present invention.
Figure 17A:
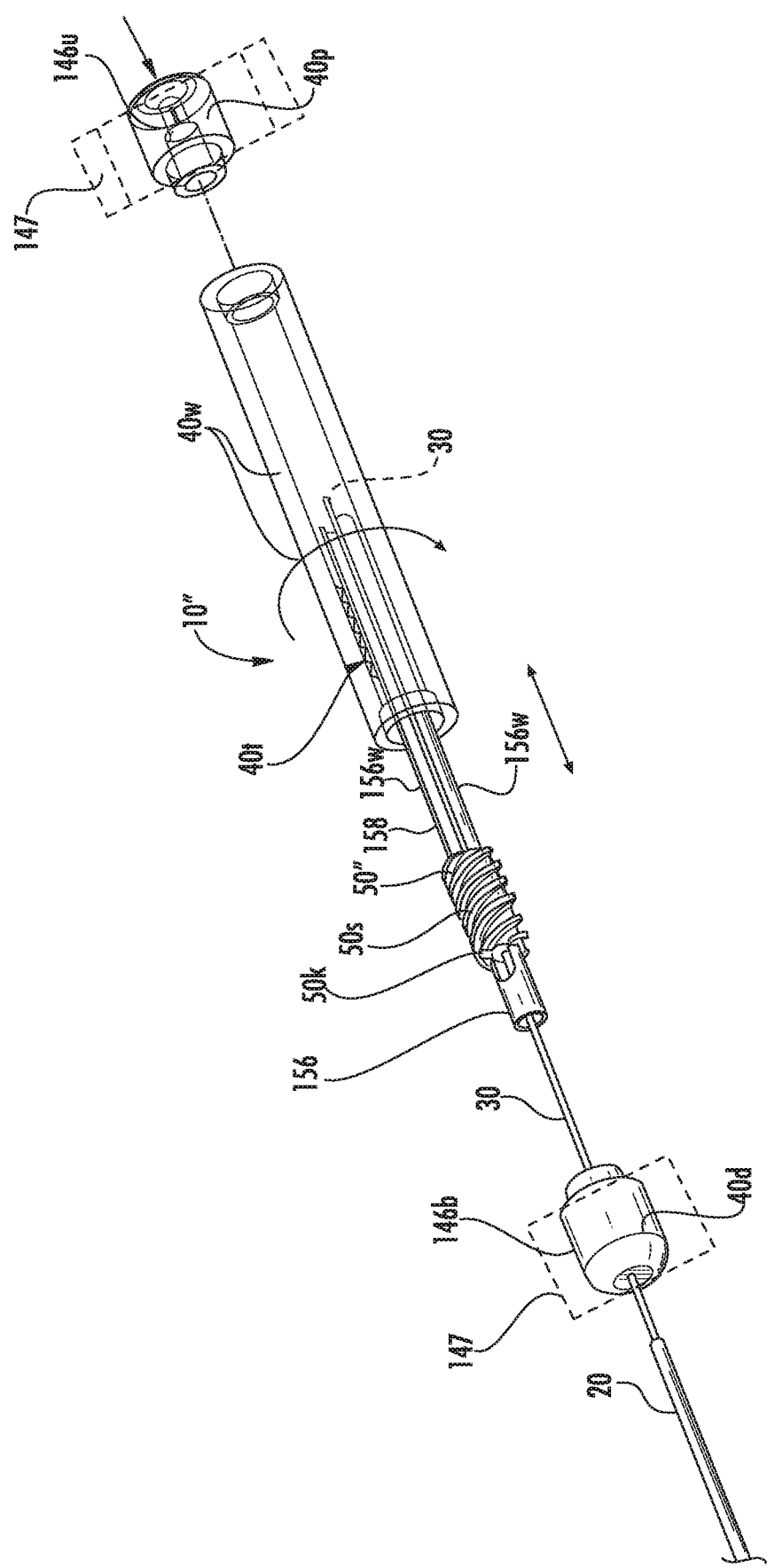
Figure 11B:
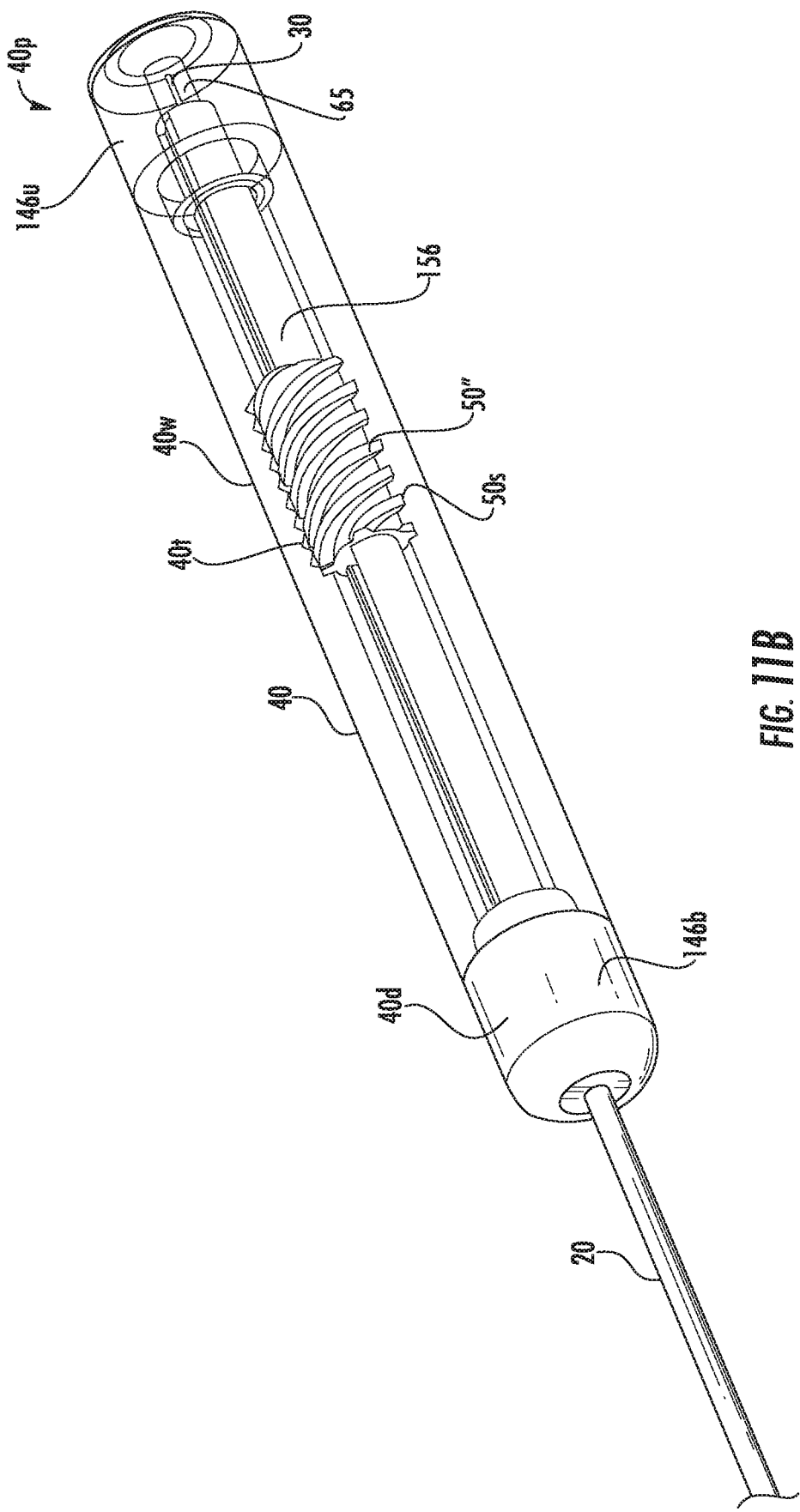
FIG. 11B is a greatly enlarged partial assembly view of the portion of the intrabody fluid transfer assembly shown in FIG. 11A.

FIGS. 9G, 9H and 9I illustrate exemplary attachment configurations of components of the assembly 10'. The pin 153 can be affixed, typically bonded, to the gear 150. The proximal end of the tubular cannula 20p can be bonded or otherwise affixed to the distal end of the housing 40d. The gear 150 can be affixed, typically bonded, to the needle 30, typically the inner capillary 31. The needle 30 can extend through and out each end of the gear 150, typically via a longitudinally extending medial slot, channel or aperture in the gear 150. The housing members 40a, 40b can be matably attached, typically bonded, with the gear 150 and needle 30, typically the inner capillary 31, therein.

The tube 65, attached to the screw 50s and the needle 30 (i.e., inner capillary 31) can form a unitary assembly so that the screw 50s, tube 65 and needle 30 can move as a unit in the housing 40 to extend and retract the needle tip 30t.

FIGS. 10A, 10B, 11A and 11B illustrate another embodiment of the assembly 10". In this embodiment, similar to the embodiment shown in FIG. 1A, the outer wall 40w of the housing 40 can rotate to engage the length adjustment mechanism 50" which can comprise a longitudinally extending internal screw 50s. The internal wall can comprise threads 40t that engage the internal screw 50s so that when a user rotates the outer wall 40w (i.e., a cylindrical "knob"), the screw 50s moves longitudinally up and down. In some embodiments, the screw 50s is bonded or otherwise affixed to the needle 30 and does not rotate to move the needle 30 up and down relative to the tubular cannula 20. The housing 40 can have upper and lower members 146u, 146b that are static and do not rotate or move in a longitudinal direction. In operation, a user can hold onto one or both of these members 146u, 146b and rotate the intermediate outer wall segment 40w to move the screw 50s up or down and therefore move the needle 30 up or down relative to the tubular cannula 20. A proximal end of the tubular cannula 20p can terminate inside of and typically at a distal end of the housing 40d.

Referring to FIG. 11A, the screw 50s can be held by a hollow internal tubular shaft 156 that can guide the screw 50s up and down in the housing 40. The shaft 156 can have a wall 156w that has an open longitudinally extending segment 158. The open segment can extend circumferentially between about 15 to about 90 degrees. The shaft 156 can connect/attach to the upper and lower stationary members 146u, 146b. The longitudinally extending open segment 158 can be a cut out that is keyed to a matable internal anti-rotation feature. The screw 50s can have a radially extending key feature 50k that can engage a slot in the housing 40 to provide anti-rotational support.

Referring again to FIG. 11A, the upper and/or lower member 146u, 146b can have user-tactile engagement features 147 such as be knurled, have a raised surface pattern and/or have a larger outer dimension or feature (i.e., greater diameter, finger engagement member such as a projection or fin or body with a larger radial or lateral extent) relative to the rotatable cylindrical outer wall segment 40w that can provide ease of user touch and hold during use.

FIGS. 12A-12D also illustrate that the fluid transfer assembly 10" can include a tube 65 that encloses the needle 30 and that extends above the housing 40 to a connector 60, typically a luer connector as discussed above.

Figure 12A:
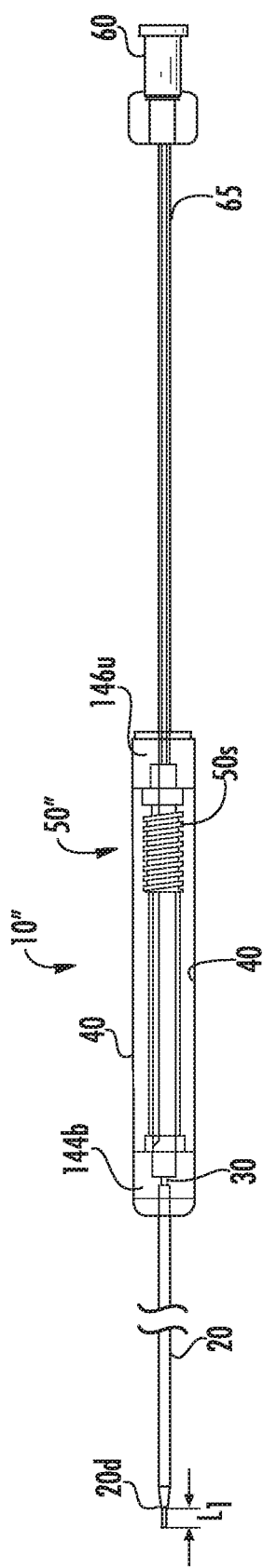
FIG. 12A is a side partially exposed view of the infusion assembly shown in FIG. 10A illustrating a needle tip to tubular cannula retracted configuration with the gear outside the housing according to embodiments of the present invention.
Figure 12B:
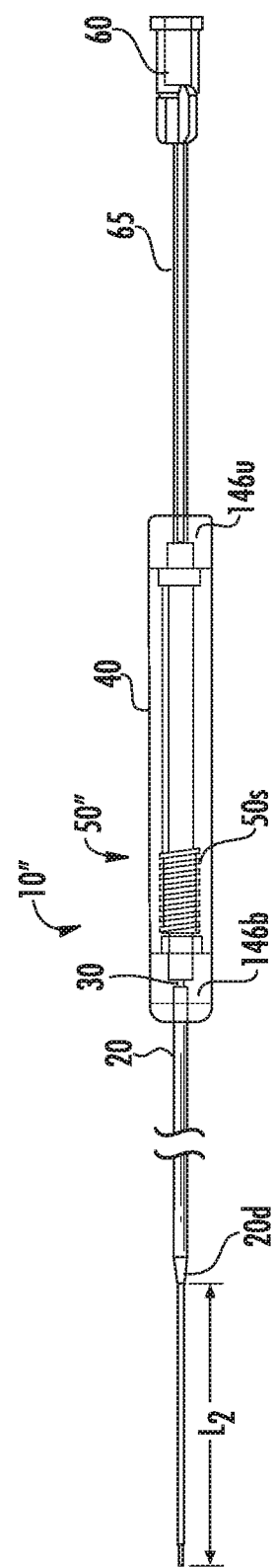
FIG. 12B is a side partially exposed view of the infusion assembly shown in FIG. 12A illustrating a needle tip to tubular cannula extended configuration with the gear inside the housing according to embodiments of the present invention.

Referring to FIGS. 12A-12D, the screw 50s can reside closer to the distal end of the housing 40d when the needle tip 30t is extended, compare, for example, FIGS. 12B-12D with the retracted configuration shown in FIG. 12A.

FIGS. 12E and 12F illustrate exemplary attachment configurations of components of the assembly 10". The tube 65 can be attached to an upper end of the screw 50s and can reside in the support shaft 156. The opposing ends of the support shaft 156 can be affixed to the respective upper and lower members 146u, 146b of the housing 40.

Optionally, the needle 30 can travel longitudinally maximally a stroke distance between extended and retracted positions between 1-6 inches, such as between 2-4 inches, while the tubular cannula 20 is fixed in its length relative to the needle and/or housing 40.

Figure 13:
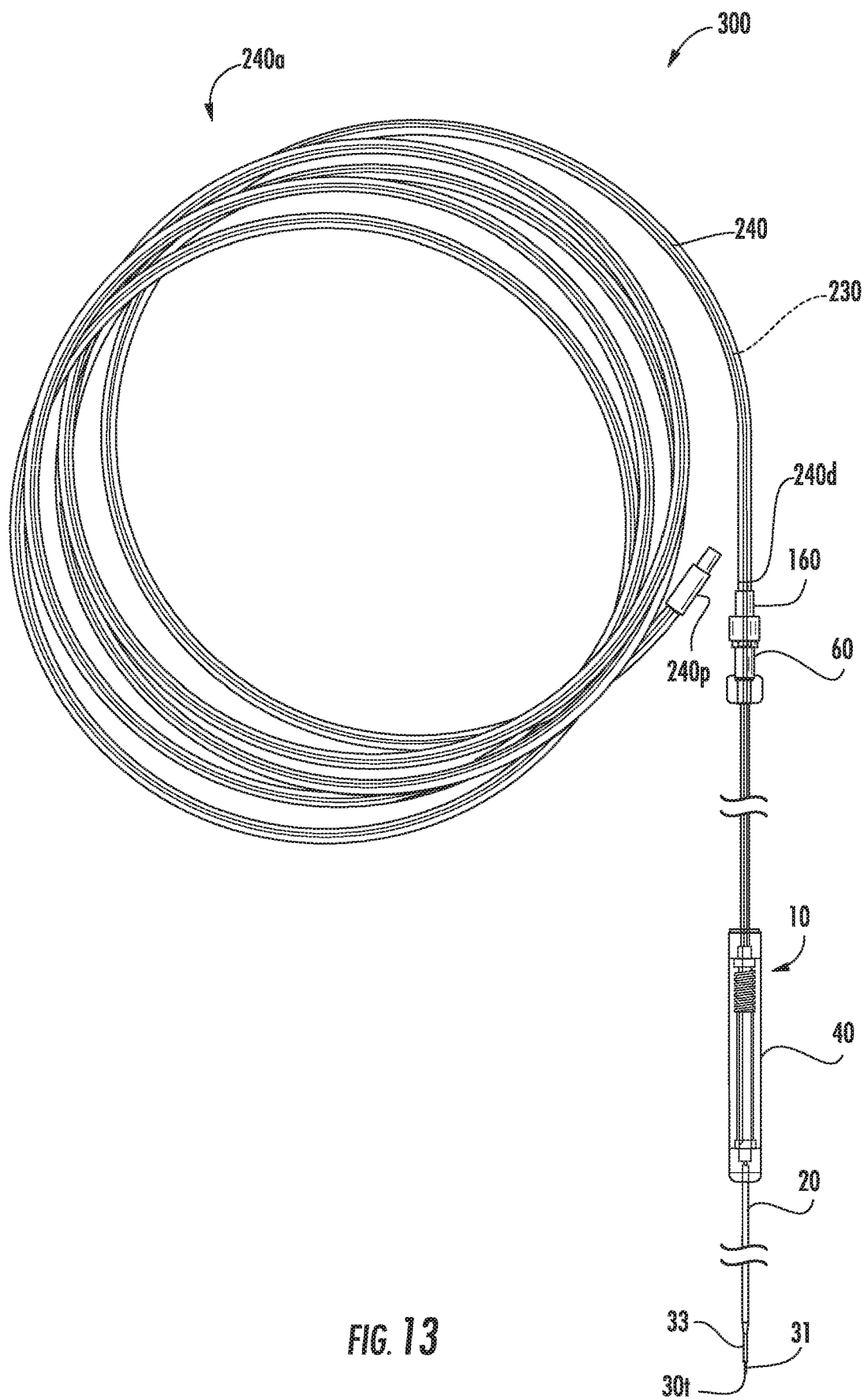
FIG. 13 is a top view of an exemplary intrabody fluid transfer assembly according to embodiments of the present invention.

Referring to FIG. 13, in some embodiments, the assembly 10, 10', 10" can be used with a length of flexible (extension) tubing 240 which may be provided as an integrated subassembly 240a. In other embodiments, the tubing 240 can be provided as a component separate from the assembly 10, 10', 10" for assembly prior to or during a procedure. If so, the ends of the tubing 240 and/or connectors 60 and 160 may be capped or held in sterile sleeves or otherwise package to maintain sterility or cleanliness.

In some embodiments, a length of the needle 30 or a cooperating (fused silica) capillary tube 230 can be enchased in the flexible tubing 240. The length may be a short or long length. The flexible tubing 240 can protect a long length of the proximal end of the needle 30, the length above and outside the housing 40, or another downstream cooperating needle and/or capillary 230 attached thereto where such a configuration is used.

In some embodiments, the long needle segment 230 can be one continuous piece of fused silica glass that goes from the distal end 240d of the tubing 240 at the connector 160 to the very proximal end 240p, typically between about 4 feet to about 10 feet long. The tubing 240 with the capillary/ needle segment 230 can be used to connect the needle 30 to the pump P (FIG. 9) or other pressurized source and the delivery substance A can flow through the tubing 240 to the needle 30 for delivery. Further, other MRI compatible needle materials may be used. According to some embodiments, the tubing 240 is flexible PVC tubing. According to some embodiments, the tubing 240 is silicone tubing. The tubing 240 may have various lengths. For example, in some embodiments, the tubing may be between about four to about ten feet (4 ft-loft) in length, although other lengths are possible.

The tubular cannula 20 can have a rigid body. The cannula 20 may comprise alumina/ceramic that can be MRI visible. The cannula 20 can have an outer surface having a lubricious coating and/or sleeve 23. The coating and/or sleeve can be a substantially transparent polymeric material. Where a sleeve is used, the sleeve 23 can be a thin flexible polymeric sleeve that can be conformably attached to the underlying cannula body. The coating and/or sleeve can be configured with sufficient strength to be able to retain components of the cannula should the cannula fracture. The sleeve can be an elastomeric shrink wrap or tube that can be heat-shrink applied to the underlying body.

The assembly 10, 10', 10" can be configured to flowably introduce and/or inject a desired therapy substance (e.g., antigen, gene therapy, chemotherapy or stem-cell or other therapy type).

The connector 160 can be configured as a luer lock to lock to the connector 60 and the needle/tubing 240/230 can be operatively coupled to an infusion pump P which supplies a mass flow of the desired substance or material to be delivered into the patient.

Figure 14:
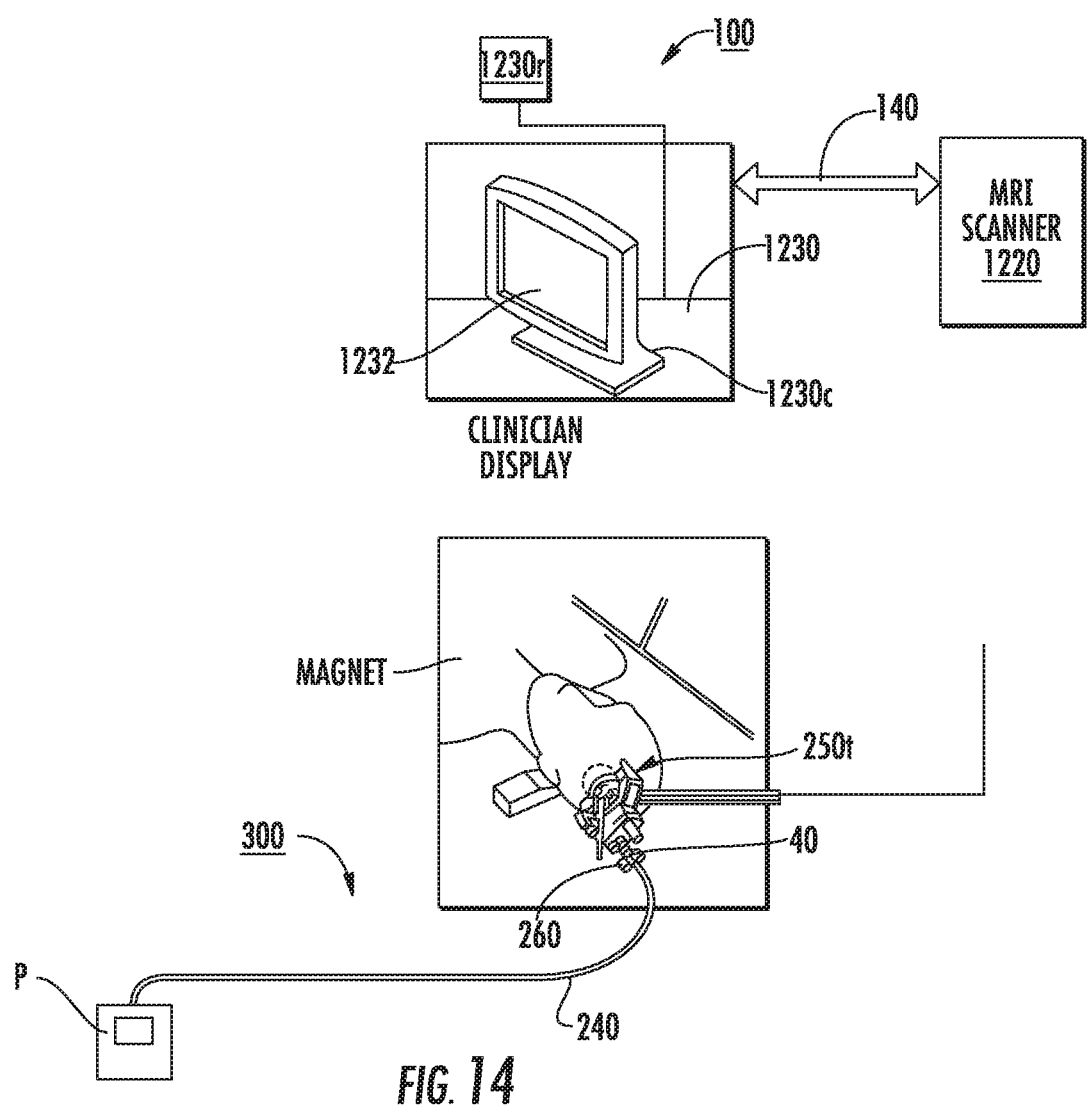
FIG. 14 is a schematic illustration of an MRI-guided interventional system in which embodiments of the present invention may be utilized.
Figure 15:
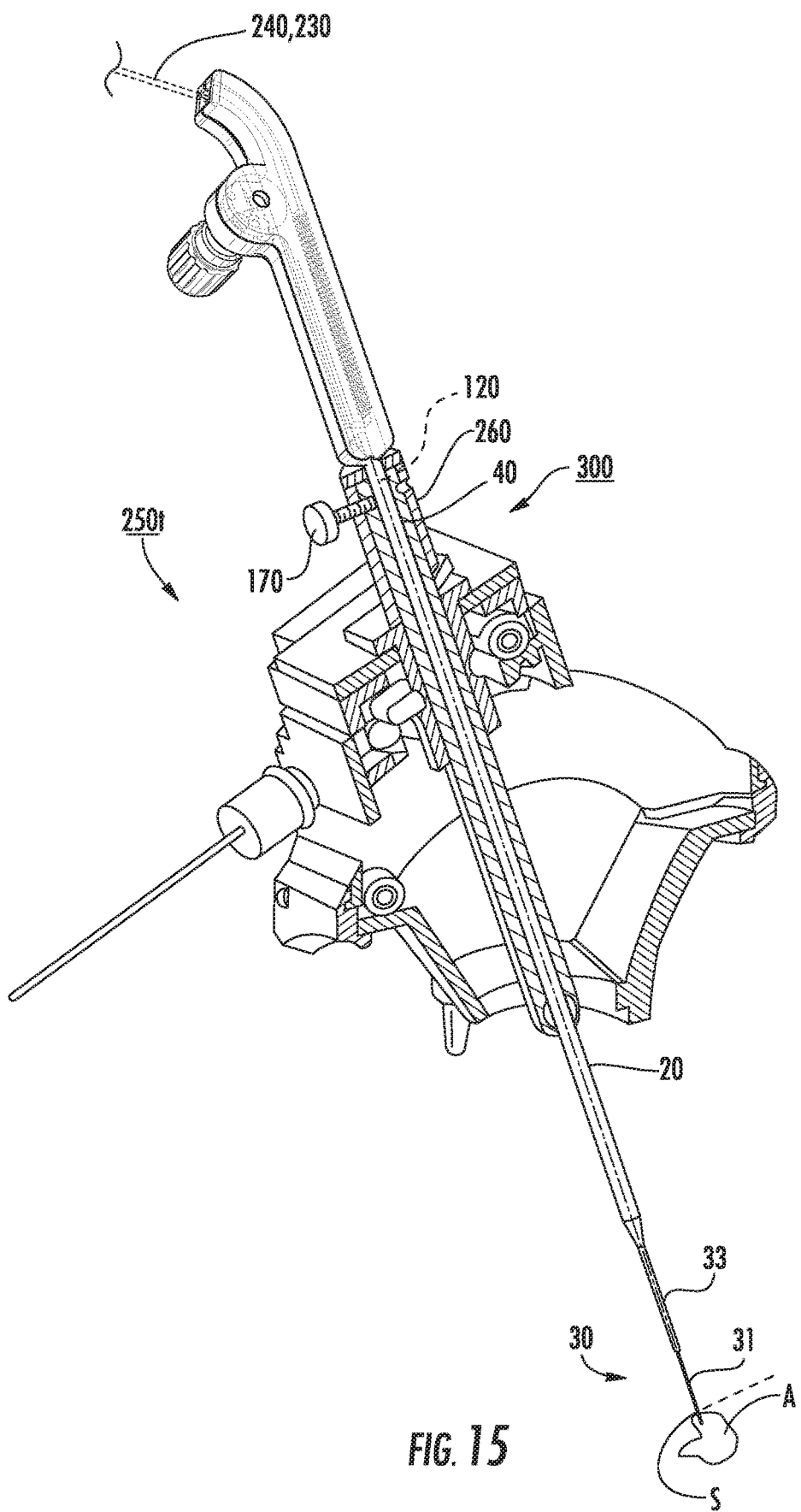
FIG. 15 is a sectional view of the trajectory guide of the MRI-guided system of FIG. 14 with an exemplary needle and surgical cannula for transferring a substance (e.g., an infusate, etc.) to an intrabody target region of a patient.

As shown in FIGS. 14 and 15, the tubular cannula 20 can extend through a tubular support 260 of a trajectory guide 250t that can be held by a base or frame, e.g., a stereotactic frame that can be secured to the patient or that can be secured to a holder residing over the patient. See, e.g., U.S. Pat. Nos. 8,315,689, 8,175,677 and 8,374,677 and US Patent Application Publication No. 2010/0198052 (Ser. No. 12/694,865) for descriptions of patient planning and entry protocols and frames and trajectory guides, the contents of which are hereby incorporated by reference as if recited in full herein.

In some embodiments, the needle 30 is configured to deliver a drug therapy to the brain. The drug therapy can comprise substance S (FIG. 15) delivered to the target site or region A through the tubular cannula 20 and cooperating needle 30 may be any suitable and desired substance for drug discovery, animal or human clinical trials and/or approved medical procedures. According to some embodiments, the substance S is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dentritic cells). The dentritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance S may comprise radioactive material such as radioactive seeds. Substances S delivered to a target area in accordance with embodiments of the present invention may include, but are not limited to, the following drugs (including any combinations thereof) listed in Table 1:

TABLE 1

| DRUG (generic name) | DISORDER(S) |
| --- | --- |
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |

TABLE 1-continued

| DRUG (generic name) | DISORDER(S) |
|---|---|
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |

TABLE 1-continued

| DRUG (generic name) | DISORDER(S) |
|---|---|
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| 1-methylfolate | Depression & BPD |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |
| Thioridazine | Schizophrenia & Psychosis |
| Cytarabine | Chemotherapy, hematological malignancies |

According to some embodiments, the assembly 10, 10', 10" is configured as an infusate delivery system that is delivered to a patient at an infusion rate in the range of from about 1 to 3 µL/minute.

Insertion of the surgical tubular cannula 20 (or any other surgical, e.g., delivery, cannula) can be tracked in near real time by reference to a void in the patient tissue caused by the cannula 20 and reflected in the MR image. In some embodiments, one or more MRI-visible fiducial markers may be provided on the surgical cannula 20 or housing 40, MR scanned and processed, and displayed on the UI. In some embodiments, the surgical cannula 20 may itself be formed of an MRI-visible material, MR scanned and processed, and displayed on the UI.

According to some embodiments, the surgical cannula 20 may include an embedded intrabody MRI antenna that is configured to pick-up MM signals in local tissue during an MRI procedure. The MRI antenna can be configured to reside on a distal end portion of the surgical cannula. In some embodiments, the antenna has a focal length or signal-receiving length of between about 1-5 cm, and typically is configured to have a viewing length to receive MM signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

While the surgical cannula 20 and needle 30 have been described by way of example as delivery devices and methods for delivering a substance to a patient, in accordance with some embodiments of the invention, the cannula 20 and needle 30 and associated methods can be used to withdraw a substance (e.g., spinal fluid, cardiac fluid or neuro fluid) from a patient. Thus, it will be appreciated that the devices and methods as disclosed herein can be used to transfer a substance into and/or from a patient.

While the devices have been described herein primarily with reference to MRI-guided insertion and infusion procedures, in some embodiments the devices can be used in procedures without MRI guidance.

While the surgical tubular cannula 20 has been described in use with a trajectory guide 250*t*, the cannula 20 may be used with other types of trajectory guidance or stereotactic frames or without a stereotactic frame or trajectory guide.

FIG. 14 illustrates an MRI-guided interventional system 100 with an MRI scanner 1220, a clinician workstation 1230 with at least one circuit 1230*c*, at least one display 1232, an MRI compatible trajectory guide 250*t* and a fluid transfer assembly 300 (including the assembly 10, 10', 10" and tubing 240 (FIG. 13). In some embodiments, the fluid exchange (i.e., delivery) assembly 300 can cooperate with an automated infusion pump P or, less preferably, a manual syringe, or another pressurized delivery source.

The system 100 can be configured to render or generate near real time or real time visualizations of the target anatomical space using MRI image data and predefined data of at least one surgical tool (e.g., tubular cannula 20, housing 40 and/or trajectory guide 250*t*) to segment the image data and place the trajectory guide 250*t* and the cannula 20 in the rendered visualization in the correct orientation and position in 3D space (which is the MRI surgical space for MM embodiments), anatomically registered to a patient. The trajectory guide 250*t* and the cannula 20 can include or cooperate with tracking, monitoring and/or other interventional components.

An exemplary trajectory guide 250*t* is illustrated in FIG. 14 in an exemplary (head) position on a patient. However, the trajectory guide can be used for any target location including, for example, the spine. The trajectory guide 250*t* can be mounted over or on an object, e.g., patient or subject, so that the upper receiving tube/support column 260 (FIG. 15) is oriented substantially perpendicular to the entry location (typically for spinal uses) or may be mounted to extend outward from the patient entry location at an angle as shown in FIG. 14.

The trajectory guide 250*t* typically provides X-Y adjustment and pitch and roll adjustment in order to accurately position the cannula 20 at a desired location within a patient. For additional discussion of examples of suitable trajectory guides, see U.S. Pat. No. 8,374,677, the contents of which are hereby incorporated by reference as if recited in full herein. However, it is noted that other trajectory guide configurations may be used and embodiments of the invention are not limited by the examples of the trajectory guides herein.

According to some embodiments, the systems are configured to provide a substantially automated or semi-automated and relatively easy-to-use MRI-guided system with defined workflow steps and interactive visualizations. In particular embodiments, the systems define and present workflow with discrete steps for finding target and entry point(s), guiding the alignment of the targeting cannula to a planned trajectory, monitoring the insertion of the tubular (guide) cannula 20, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

The system 100 may also include a decoupling/tuning circuit that allows the system to cooperate with an MRI scanner 1220 and filters and the like. See, e.g., U.S. Pat. Nos. 6,701,176; 6,904,307 and U.S. Patent Application Publication No. 2003/0050557, the contents of which are hereby incorporated by reference as if recited in full herein.

Figure 16:
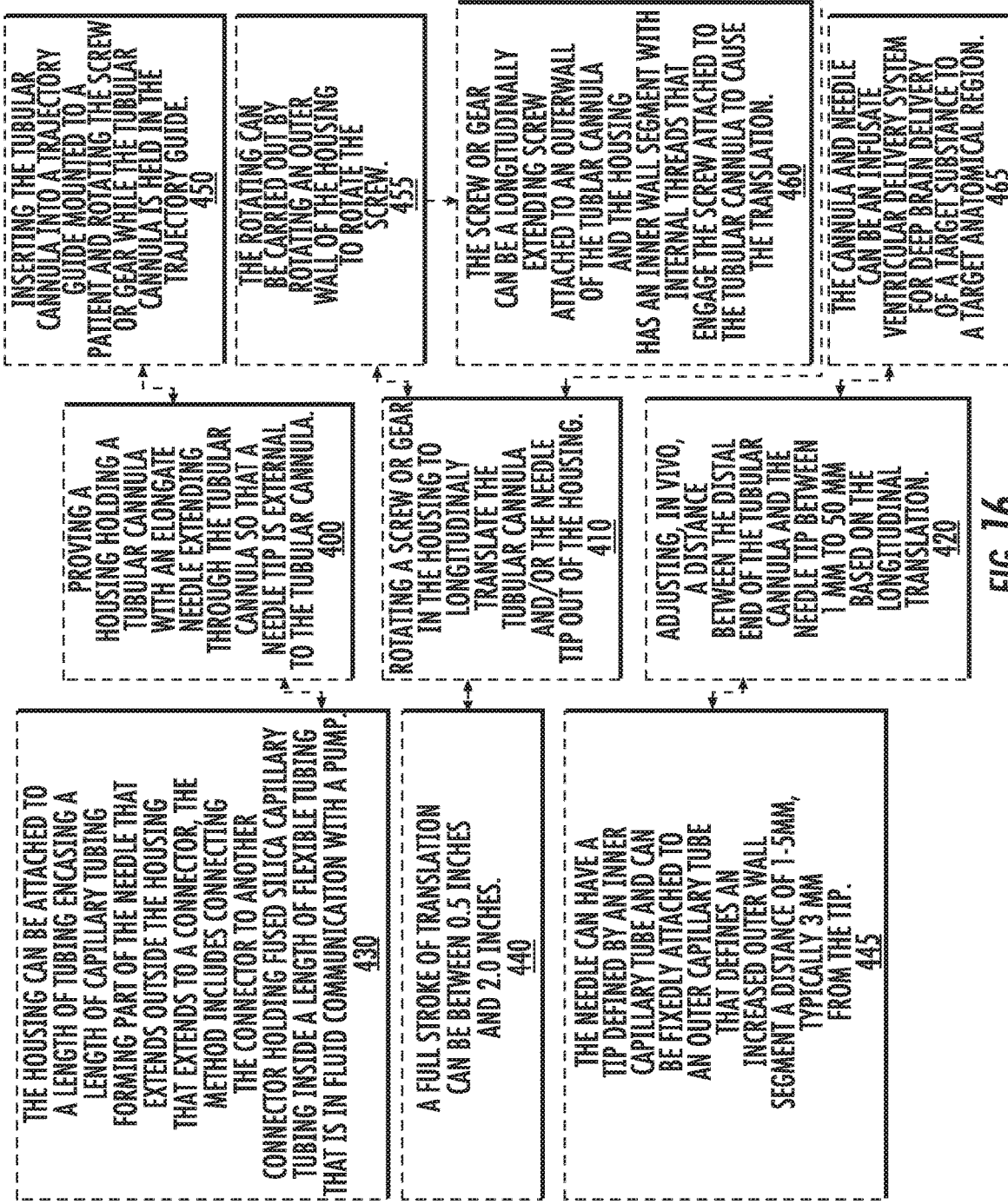
FIG. 16 is a flow chart of exemplary actions that can be carried out according to embodiments of the present invention.

FIG. 16 is a flow chart of exemplary actions that can be carried out according to embodiments of the present invention. A housing holding a tubular cannula with an elongate needle extending through the tubular cannula is provided so that a needle tip is external to the tubular cannula (block 400). A screw or gear in the housing is rotated to longitudinally translate the tubular cannula and/or the needle tip out of the housing (block 410). Adjusting, in vivo, a distance between the distal end of the tubular cannula and the needle tip based on the longitudinal translation (block 420).

The housing can be attached to a length of tubing encasing a length of capillary tubing forming part of the needle that extends outside the housing that extends to a connector, the method includes connecting the connector to another connector holding fused silica capillary tubing inside a length of flexible tubing that is in fluid communication with a pump (block 430).

A full stroke of translation can be between 0.5 inches and 2 inches or about 1.6 inches, such as about 1.25 inches (block 440).

The needle can have a tip defined by an inner capillary tube and can be fixedly attached to an outer capillary tube that defines an increased outer wall segment a distance of 1-5 mm, typically 3 mm from the tip (block 445).

Inserting the tubular cannula into a trajectory guide mounted to a patient and rotating the screw while the tubular cannula held in the trajectory guide (block 450).

The rotating can be carried out by rotating an outer wall of the housing to rotate the screw (block 455).

The screw can be or gear can comprise a longitudinally extending screw attached to an outerwall of the tubular cannula and the housing has an inner wall segment with internal threads that engage the screw attached to the tubular cannula to cause the translation (block 460).

The screw or gear can comprise a longitudinally extending rack gear that is attached to the needle and that can move the needle relative to the tubular cannula in response to rotation of an external thumb wheel that rotates a pinion that engages the rack gear (block 462).

The cannula and needle can be an infusate ventricular delivery system for brain delivery of a target substance to a target anatomical region (block 465). For example, the device can be configured to allow a single intrabody insertion of the needle 30 to a target anatomical region in the brain (such as tissue generally in-line with and between the nose and back of the head and, starting dispensing/infusing from the back of the head while translating the needle frontward to treat a large volume through one intrabody insertion of the needle).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical assembly for transferring fluid to or from a subject, comprising:
   a tubular cannula having opposing proximal and distal ends with an open axially extending lumen;
   an elongate needle having opposing proximal and distal ends, wherein a length of the needle extends through the tubular cannula lumen so that the distal end of the needle with a tip extends out of the distal end of the distal end of the tubular cannula to provide an exposed needle tip; and
   a housing comprising opposing proximal and distal ends, wherein the housing holds the tubular cannula with the needle with the tubular cannula and needle extending out of the distal end of the housing, wherein the housing comprises an internal length adjustment mechanism that is attached to one or both of the tubular cannula or the needle and that adjusts a length between the distal end of the tubular cannula and the exposed needle tip,
   wherein the elongate needle comprises a tube that extends through the housing and the tubular cannula and defines the exposed needle tip,
   wherein the tube of the elongate needle comprises a continuous length of fused silica glass that extends out of both proximal and distal ends of the housing, wherein the distal end of the needle has a stepped configuration with a first segment having a first outer diameter that merges into a second end segment having a second smaller outer diameter having a length that extends to the tip of the needle, and wherein the needle tip extends out of the tubular cannula an adjustable distance of between about 2 mm to about 30 mm.

2. The assembly of claim 1, wherein the housing has a length from about 1 inch to about 6 inches and comprises an external rotatable member or a rotatable cylindrical outer wall that engages the length adjustment mechanism to move at least one of the needle or the tubular cannula longitudinally.

3. The assembly of claim 1, wherein the housing comprises an external thumbwheel that engages an internal gear of the length adjustment mechanism and that is attached to the tubular cannula or the needle to longitudinally move the tubular cannula or the needle to adjust the length, and wherein the tubular cannula is an outer tubular cannula with a tapered distal end portion, and wherein the exposed needle tip is configured to always be outside of the tubular cannula.

4. The assembly of claim 1, wherein the length adjustment mechanism comprises an internal screw, and wherein the housing comprises a rotatable outer wall, and wherein, in response to rotation of the outer wall of the housing, the internal screw longitudinally translates to adjust the length between the distal end of the tubular cannula and the exposed tip of the needle.

5. The assembly of claim 4, wherein the needle has a stroke distance of between about 0.5 inches and 3 inches and has a proximal end that extends a length outside a proximal end of the housing.

6. The assembly of claim 1, wherein the housing holds a longitudinally extending screw of the length adjustment mechanism in the housing that is in communication with the rotatable outer wall that can move longitudinally in response to the rotation of the outer wall to adjust the length between the distal end of the tubular cannula and the needle tip.

7. The assembly of claim 1, wherein the tube extends a distance above the proximal end of the housing and through the housing to define the exposed needle tip, the assembly further comprising a luer connector attached to the tube above the proximal end of the housing.

8. The assembly of claim 1, wherein the tubular cannula has an outer polymeric coating and/or sleeve, wherein a distal end of the tubular cannula is tapered so that it has a smaller outer diameter at a tip of the tubular cannula relative to an outer diameter rearward of the tip of the tubular cannula, and wherein a proximal end of the tubular cannula terminates inside the housing.

9. The assembly of claim 1, wherein an outer surface of the tubular cannula has a size and geometry adapted for use with a stereotactic frame with a trajectory guide having a support column sized and configured to releasably hold the tubular cannula so that the housing resides above the support column, and wherein the needle has an inner diameter of between about 100 μm to about 750 μm.

10. A surgical assembly for transferring fluid to or from a subject, comprising:
    a tubular cannula having opposing proximal and distal ends with an open axially extending lumen;
    an elongate needle having opposing proximal and distal ends, wherein a length of the needle extends through the tubular cannula lumen so that the distal end of the needle with a tip extends out of the distal end of the distal end of the tubular cannula to provide an exposed needle tip;
    a housing comprising opposing proximal and distal ends, wherein the housing holds the tubular cannula with the needle with the tubular cannula and needle extending out of the distal end of the housing, wherein the housing comprises an internal length adjustment mechanism that is attached to one or both of the tubular cannula or the needle and that adjusts a length between the distal end of the tubular cannula and the exposed needle tip;
    wherein the elongate needle comprises a tube that extends through the housing and the tubular cannula and defines the exposed needle tip, and wherein the tube extends a distance above the proximal end of the housing:
    a luer connector attached to the tube above the proximal end of the housing;
    and flexible tubing encasing the tube above the housing, attached to a proximal end of the housing and the luer connector.

11. A surgical assembly for transferring fluid to or from a subject, comprising: a tubular cannula having opposing proximal and distal ends with an open axially extending lumen; an elongate needle having opposing proximal and distal ends, wherein a length of the needle extends through the tubular cannula lumen so that the distal end of the needle with a tip extends out of the distal end of the distal end of the tubular cannula to provide an exposed needle tip; and a housing comprising opposing proximal and distal ends, wherein the housing holds the tubular cannula with the needle with the tubular cannula and needle extending out of the distal end of the housing, wherein the housing comprises an internal length adjustment mechanism that is attached to one or both of the tubular cannula or the needle and that adjusts a length between the distal end of the tubular cannula and the exposed needle tip, wherein a distal end of the tubular cannula is tapered so that it has a smaller outer diameter at a tip of the tubular cannula relative to an outer diameter rearward of the tip of the tubular cannula, and wherein a proximal end of the tubular cannula terminates inside the housing,
- wherein the elongate needle comprises a tube that extends through the housing and the tubular cannula and defines the exposed needle tip,
- and wherein the tubular cannula comprises a ceramic material and a conformal outer polymeric sleeve,
- wherein the tube is an inner tube that is bonded to an outer tube over a longitudinally extending length inside the housing and tubular cannula and a length that can be external to the tubular cannula that define at least first and second co-axially disposed external segments having different outer diameters, with a smallest sized outer diameter of the first segment extending to the needle tip, and wherein the outer tube comprises a conformal outer polymeric sleeve residing at least at an interface between the distal end of the tubular cannula and the outer tube to contact an inner surface of the tubular cannula when retracted therein to thereby inhibit fluid intake thereat.

12. The assembly of claim 11, wherein the outer tube terminates inside the housing while the inner tube extends out of the housing proximal end.

13. A surgical assembly for transferring fluid to or from a subject, comprising:
- a tubular cannula having opposing proximal and distal ends with an open axially extending lumen;
- an elongate needle having opposing proximal and distal ends, wherein a length of the needle extends through the tubular cannula lumen so that the distal end of the needle with a tip extends out of the distal end of the distal end of the tubular cannula to provide an exposed needle tip; and
- a housing comprising opposing proximal and distal ends, wherein the housing holds the tubular cannula with the needle with the tubular cannula and needle extending out of the distal end of the housing, wherein the housing comprises an internal length adjustment mechanism that is attached to one or both of the tubular cannula or the needle that adjusts a length between the distal end of the tubular cannula and the exposed tip of the needle,
- wherein the length adjustment mechanism comprises a flexible rack gear that is configured to longitudinally reciprocate relative to the housing and at least partially extend out of the housing and retract into the housing to adjust the length, wherein the flexible rack gear has sufficient rigidity to have a self-supporting three dimensional shape but flexes from a straight longitudinally extending orientation inside the housing to a curvilinear orientation when outside the housing, and wherein the needle is coupled to and extends through the flexible rack gear to extend out of opposing proximal and distal ends of the flexible rack gear.

14. A surgical assembly for intrabody fluid transfer, comprising:
- a tubular cannula having opposing proximal and distal ends with an open axially extending lumen, wherein a distal end portion of the tubular cannula is tapered so that it has a smaller outer diameter at a tip of the tubular member relative to an outer diameter of the tubular member closer to the housing;
- an elongate needle having opposing proximal and distal ends, wherein a length of the needle extends through the tubular cannula lumen so that the distal end of the needle with a tip extends out of the distal end of the distal end of the tubular cannula to provide an exposed needle tip, wherein the exposed needle tip is configured to always remain outside the tip of the tubular cannula;
- a housing comprising opposing proximal and distal ends and a rotatable external member or a rotatable outer wall that holds the tubular cannula with the needle with the tubular cannula and needle extending out of the distal end of the housing; and
- a length adjustment mechanism in communication with the rotatable external member or the rotatable outer wall that moves the needle or the tubular cannula longitudinally to extend and retract the distal end of the needle relative to the tubular cannula, wherein the rotatable external member or the rotatable outer wall is configured to cooperate with the length adjustment mechanism to adjust a length between the distal end of the tubular cannula and the exposed tip of the needle,
- wherein the length adjustment mechanism comprises a flexible rack gear that extends in a longitudinal direction in the housing and that has sufficient rigidity to have a self-supporting three dimensional shape but that can flex when outside the housing, wherein the flexible rack gear is configured to longitudinally reciprocate relative to the housing, and wherein the needle is coupled to and extends through and out of opposing proximal and distal ends of the flexible rack gear.

15. The assembly of claim 14, wherein the length adjustment mechanism comprises a pinion gear in communication with the rotatable external member and a longitudinally extending rack gear that engages the pinion gear that moves the needle or the tubular cannula longitudinally without rotation of the needle or the tubular cannula.

16. The assembly of claim 14, wherein the needle comprises an inner tube that extends a distance above the proximal end of the housing and through the housing to the needle tip to define the needle tip, the assembly further comprising a luer connector attached to the inner tube above the proximal end of the housing.

17. A method of transferring a substance to and/or from a patient, the method comprising:
- providing a housing having opposing proximal and distal ends, the housing holding a proximal end of a tubular cannula therein with a distal end of the tubular cannula extending out of the housing, the tubular cannula having an axially extending interior lumen holding an elongate needle with a length sufficient to have a tip of the needle outside the distal end of the tubular cannula and an upper end extending out of the proximal end of the housing;
- inserting the distal end of the tubular cannula and needle into a patient; then
- transferring a substance to or from a target site through a needle lumen at the tip of the needle;
- adjusting a length between the distal end of the tubular cannula and needle tip during the transferring action; and
- wherein the adjusting the length is carried out using a length adjustment mechanism comprising a flexible rack gear fixedly attached to a sub-length of the needle above the distal end of the housing, and wherein the needle extends through the flexible rack gear and extends out of opposing proximal and distal ends of the flexible rack gear.

18. The method of claim 17, wherein the needle is an infusion needle, and wherein the transferring the substance to or from the target site is carried out by infusing a substance.

19. The method of claim 17, wherein the target site is the brain, and wherein the inserting, transferring and adjusting steps are carried out while the patient is in a magnetic field of an MRI Scanner, wherein the rack gear is held in a straight longitudinally extending orientation when inside the housing, and wherein the method comprises bending the rack gear up, down or side-side when outside the housing, and inside a bore of the MRI Scanner.

20. The method of claim 17, wherein the adjusting is carried out by extending the needle a distance out of a distal end of the tubular cannula while the tubular cannula is held at a fixed length by rotating an outer wall of the housing.

21. The method of claim 17, wherein the adjusting is carried out by extending the needle a distance out of a distal end of the tubular cannula while the tubular cannula is held at a fixed length by rotating an outer thumbwheel to rotate a pinion gear to longitudinally translate rack gear held at least partially inside the housing with the rack gear fixedly attached to the needle.

22. The method of claim 17, wherein the rack gear is held in a straight longitudinally extending orientation when inside the housing, and wherein the method comprises bending the rack gear up, down or side-side when exposed to the environment outside the housing while holding a length of the needle in the rack gear during the adjusting step.

23. A surgical assembly for intrabody fluid transfer, comprising:
a tubular cannula having opposing proximal and distal ends with an open axially extending lumen;
an elongate needle having opposing proximal and distal ends, wherein a length of the needle extends through the tubular cannula so that the distal end of the needle extends out of the distal end of the tubular cannula to provide an exposed needle tip;
a housing comprising opposing proximal and distal ends and a rotatable external member or a rotatable outer wall that holds the tubular cannula with the tubular cannula and needle extending out of the distal end of the housing;
a length adjustment mechanism in communication with the rotatable external member or the rotatable outer wall that moves at least one of the needle or the tubular cannula longitudinally to extend and retract the distal end of the needle relative to the tubular cannula to adjust a length between the distal end of the tubular cannula and the exposed tip of the needle;
wherein the needle is defined by an inner tube bonded to an outer tube to define at least first and second co-axially disposed segments having different outer diameters, with the inner tube being longer than the outer tube and defining the exposed needle tip; and
wherein the inner tube is directly affixed to the internal length adjustment mechanism.

24. The surgical assembly of claim 23, wherein the length adjustment mechanism comprising a longitudinally extending flexible rack gear with longitudinally spaced apart and laterally extending gear teeth extending across an entire width dimension of the flexible rack gear, and wherein the inner tube extends longitudinally through a medial portion of the body of the rack gear and extends out of opposing proximal and distal ends of the flexible rack gear.

* * * * *

UNITED STATES PATENT AND TRADEMARK OFFICE
CERTIFICATE OF CORRECTION

PATENT NO. : 10,576,247 B2
APPLICATION NO. : 15/420685
DATED : March 3, 2020
INVENTOR(S) : Flores et al.

Page 1 of 1

It is certified that error appears in the above-identified patent and that said Letters Patent is hereby corrected as shown below:

In the Specification

Column 15, Line 10: Please correct "(4 ft-loft)" to read -- (4 ft-10 ft) --

Column 19, Line 67: Please correct "MM" to read -- MRI --

Column 20, Line 55: Please correct "MM" to read -- MRI --

Column 21, Line 34: Please correct "MM" to read -- MRI --

Signed and Sealed this
Seventh Day of July, 2020

Andrei Iancu
*Director of the United States Patent and Trademark Office*